(12) United States Patent
Woehr et al.

(10) Patent No.: US 10,543,343 B2
(45) Date of Patent: Jan. 28, 2020

(54) NEEDLE ASSEMBLIES WITH FLASHBACK INDICATOR AND RELATED METHODS

(71) Applicant: B. Braun Melsungen AG, Melsungen (DE)

(72) Inventors: Kevin Woehr, Felsberg (DE); Yi Ying Chin, Penang (MY); Hui Kuun Teoh, Penang (MY)

(73) Assignee: B. Braun Melsungen AG, Melsungen (DE)

( * ) Notice: Subject to any disclaimer, the term of this patent is extended or adjusted under 35 U.S.C. 154(b) by 244 days.

(21) Appl. No.: 14/977,521

(22) Filed: Dec. 21, 2015

(65) Prior Publication Data

US 2016/0175563 A1 Jun. 23, 2016

Related U.S. Application Data

(63) Continuation-in-part of application No. 14/581,523, filed on Dec. 23, 2014, now abandoned.

(51) Int. Cl.
*A61M 25/06* (2006.01)
*A61B 5/15* (2006.01)
*A61M 39/02* (2006.01)

(52) U.S. Cl.
CPC .... *A61M 25/0693* (2013.01); *A61M 25/0606* (2013.01); *A61M 25/0612* (2013.01); *A61B 5/1422* (2013.01); *A61M 2039/0244* (2013.01); *A61M 2207/00* (2013.01)

(58) Field of Classification Search
CPC .............. A61M 25/0693; A61M 5/158; A61M 2039/0244; A61M 25/0606; A61M 5/162; A61M 5/32; A61M 25/0612; A61B 5/1422
See application file for complete search history.

(56) References Cited

U.S. PATENT DOCUMENTS

| 4,354,491 A | 10/1982 | Marbry |
| 5,380,290 A | 1/1995 | Makower et al. |
| 5,935,109 A | 8/1999 | Donnan |

(Continued)

FOREIGN PATENT DOCUMENTS

| EP | 0875261 A2 | 11/1998 |
| JP | H10-323394 A | 12/1998 |

(Continued)

OTHER PUBLICATIONS

Patent translate: Translation of JP2012170784A1, Nov. 8, 2017.*

(Continued)

*Primary Examiner* — Nilay J Shah
(74) *Attorney, Agent, or Firm* — Klein, O'Neill & Singh, LLP

(57) ABSTRACT

Aspects of the present disclosure include needle devices in which a needle has a notch or slot. A flashback indicator is provided at least in part in the needle lumen at the notch, adjacent the notch, or partially inside and partially outside of the notch. In use, blood flow through the needle lumen is indicated at the flashback indicator. When used with a catheter tube, the flashback indicator can be viewed through the catheter tube. The needle with the notch and flashback indicator may be used with a variety of needle applications, including as catheter assemblies, indwelling assemblies, and most, if not all, over-the-needle type devices.

22 Claims, 18 Drawing Sheets

(56) References Cited

U.S. PATENT DOCUMENTS

| | | | | |
|---|---|---|---|---|
| 6,228,060 B1* | 5/2001 | Howell | ............... | A61M 39/04 604/167.01 |
| 6,616,630 B1* | 9/2003 | Woehr | ............... | A61M 5/3273 604/110 |
| 2006/0036219 A1* | 2/2006 | Alvin | ............... | A61B 5/150473 604/272 |
| 2008/0108944 A1* | 5/2008 | Woehr | ............... | A61B 5/1411 604/164.08 |
| 2009/0187147 A1 | 7/2009 | Kurth et al. | | |
| 2010/0204553 A1* | 8/2010 | Sonderegger | ..... | A61M 25/0693 600/345 |
| 2011/0190662 A1 | 8/2011 | McWeeney | | |
| 2014/0081210 A1* | 3/2014 | Bierman | ............ | A61M 25/0606 604/164.03 |

FOREIGN PATENT DOCUMENTS

| | | | | |
|---|---|---|---|---|
| JP | 2000-262628 A | 9/2000 | | |
| JP | 2002-102345 A | 4/2002 | | |
| JP | 2012-517328 A | 8/2012 | | |
| JP | 2012-170784 A | 9/2012 | | |
| JP | 2012170784 A1 * | 9/2012 | | |
| JP | 2014-73183 A | 4/2014 | | |
| JP | 2014-519907 A | 8/2014 | | |
| WO | WO 03043496 A2 * | 5/2003 | ........ | A61M 25/0693 |
| WO | WO 2005/096778 A2 | 10/2005 | | |
| WO | WO 2009/114837 A2 | 9/2009 | | |
| WO | WO 2010/093795 A1 | 8/2010 | | |
| WO | WO 2012/162677 A1 | 11/2012 | | |
| WO | WO 2012/166746 A1 | 12/2012 | | |

OTHER PUBLICATIONS

International Search Report and Written Opinion on corresponding PCT application (PCT/EP2015/081093) from International Searching Authority (EPO) dated Jul. 15, 2016.

Office Action from the Japanese Patent Office on corresponding JP application (JP2017-528831) dated May 28, 2019.

Extended European Search Report from the European Patent Office on corresponding EP application (EP18204355.4) dated Mar. 29, 2019.

Examination Report from the Australian Patent Office on corresponding AU application (AU2015370954) dated Sep. 3, 2019.

* cited by examiner

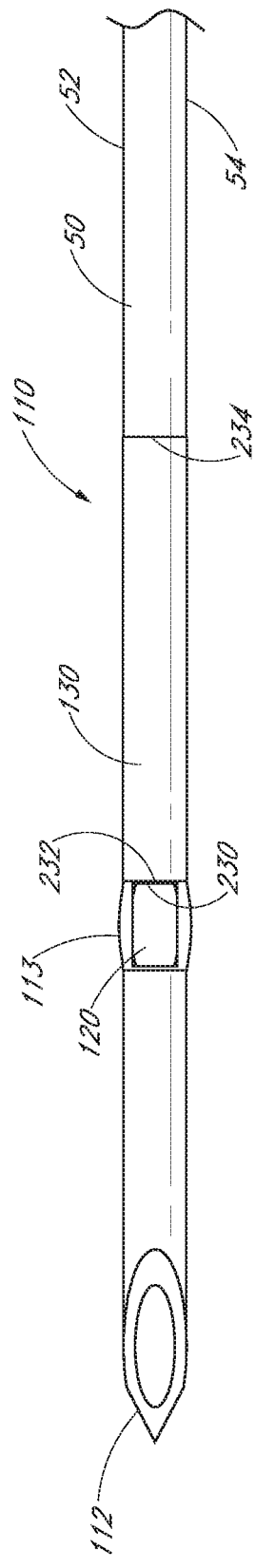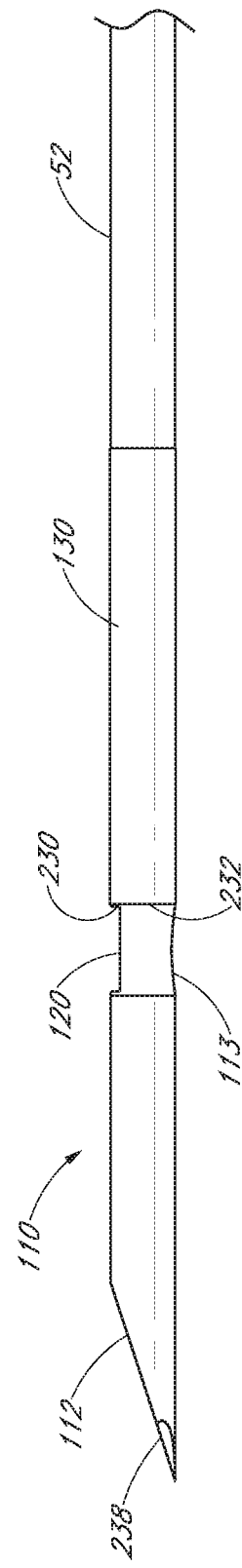
FIG. 11
FIG. 12

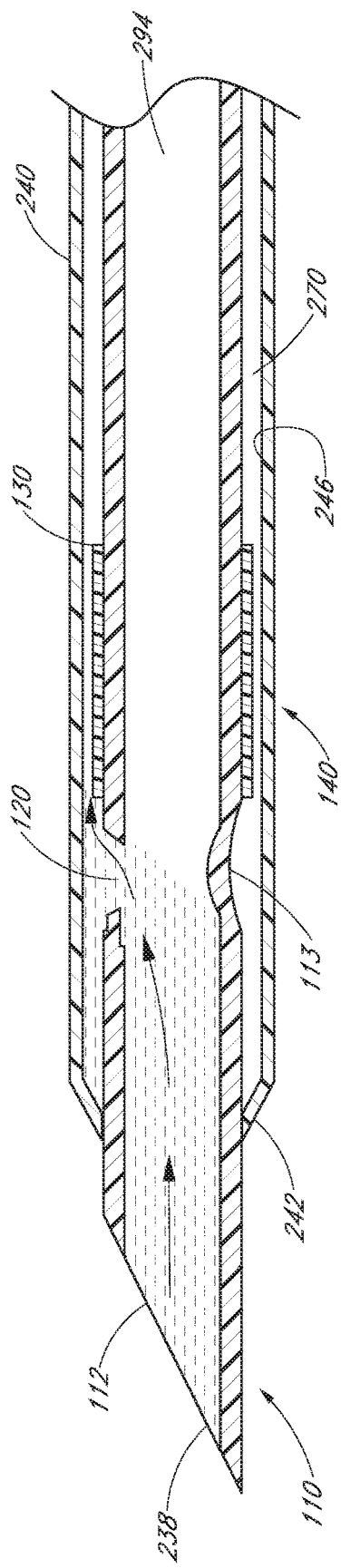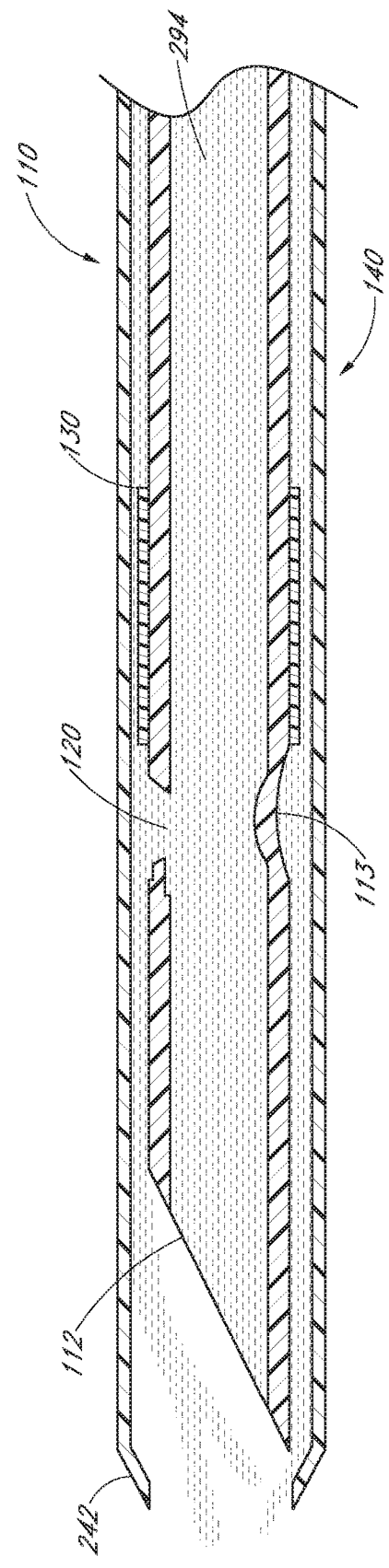
FIG. 21A
FIG. 21B

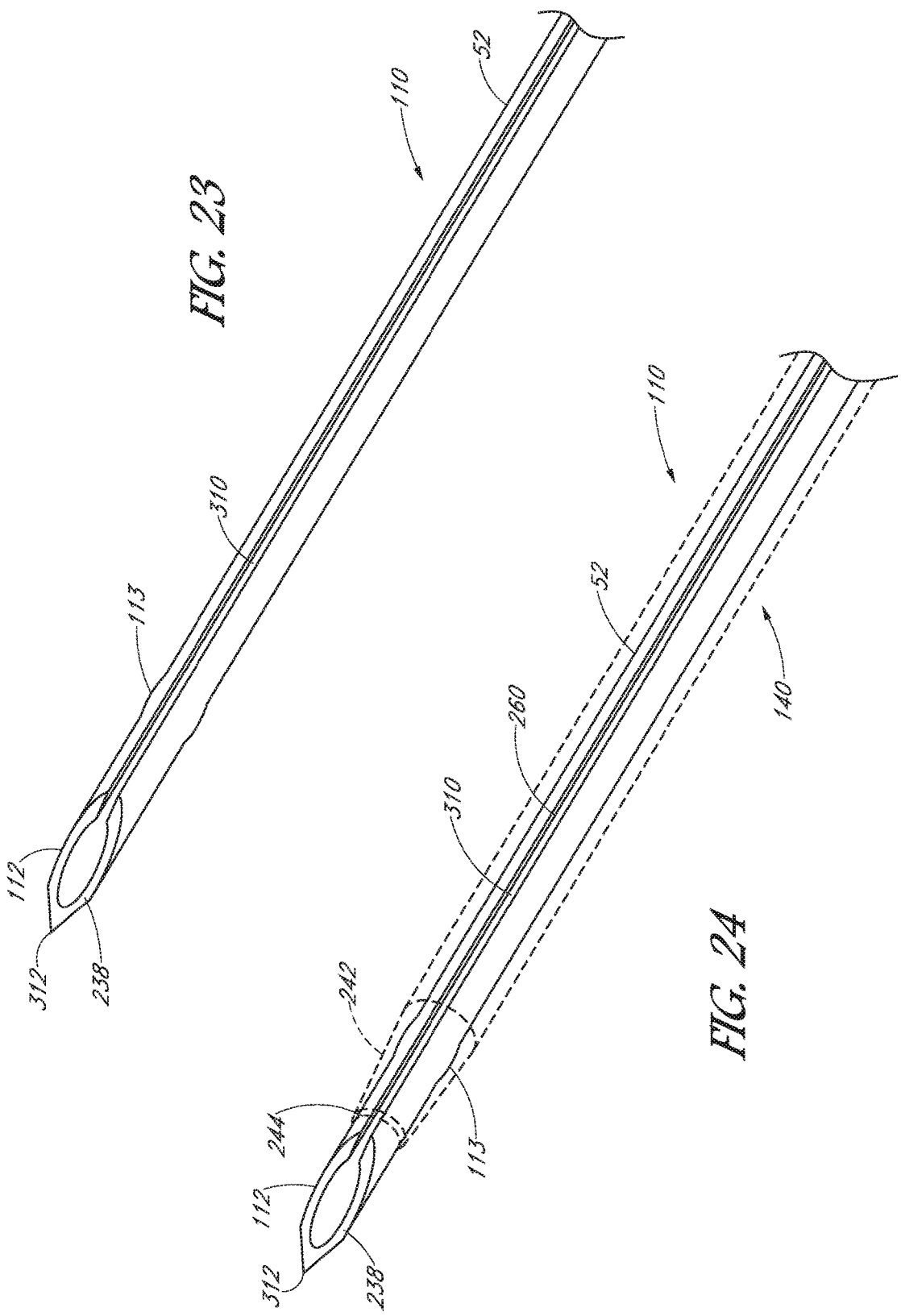

NEEDLE ASSEMBLIES WITH FLASHBACK INDICATOR AND RELATED METHODS

FIELD OF ART

The invention relates generally to needle devices, systems, and methods for use where medicines are delivered vascularly. More particularly, the present disclosure relates to catheter devices or assemblies and needle configurations used in intravenous medical devices and methods for using and making such devices and systems.

BACKGROUND

Generally, vascular access devices are used for communicating fluid with the vascular system of patients. For example, catheters are used for infusing fluid, such as normal saline solution, various medicaments, and total parenteral nutrition, into a patient, withdrawing blood from a patient, or monitoring various parameters of the patient's vascular system.

A common type of intravenous (IV) catheter is an over-the-needle peripheral IV catheter. As its name implies, an over-the-needle catheter is mounted over an introducer needle having a sharp distal tip. At least the inner surface of the distal portion of the catheter tightly engages the outer surface of the needle to prevent peelback of the catheter and thus facilitate insertion of the catheter into the blood vessel. The catheter and the introducer needle are assembled so that the distal tip of the introducer needle extends beyond the distal tip of the catheter with the bevel of the needle facing up away from the patient's skin. The catheter material can be partially transparent and can have stripes of transparent material and opaque stripes for providing x-ray contrast. The catheter and introducer needle are generally inserted at a shallow angle through the patient's skin into a blood vessel.

In order to verify proper placement of the needle and catheter in the blood vessel, the clinician generally looks for blood flashback as confirmation of the access. The first blood flashback is through the needle and into a transparent needle hub, which is sometimes referred to as primary blood flashback. This confirms at least the needle has found the vein. Then as the needle is withdrawn in a proximal direction away from the catheter tube, the blood will flash back between the needle and the catheter tube. This is sometimes referred to as secondary flashback, which confirms that the catheter tube has found the vein. Once proper placement of the catheter into the blood vessel is confirmed, the clinician may apply pressure to the blood vessel by pressing down on the patient's skin over the blood vessel distal of the introducer needle and the catheter. This finger pressure occludes the vessel, minimizing further blood flow through the catheter and possibly leaking out the catheter hub.

In some IV catheter assemblies, the needle has an open notch, through which blood can flow into the space between the needle and catheter. This "instant flash" confirms only that the needle tip has entered the vein but not necessarily that the catheter tube has entered the vein. Because there is first blood between the needle and the catheter tube when a notch is employed, a secondary flashback is not possible.

The clinician may then withdraw the introducer needle from the catheter. The introducer needle may be withdrawn into a needle tip shield or needle cap that covers the needle tip and prevents accidental needle sticks. When the needle has an open notch, the blood between the distal opening and the open notch is not held by capillary action and can drip from the needle.

Blood dripping from the open end of the needle can occur when removing the needle from the patient or the catheter hub after primary blood flashback is detected.

SUMMARY

The various embodiments of a needle safety assembly have several features, no single one of which is solely responsible for their desirable attributes. Without limiting the scope of the present embodiments as set forth in the claims that follow, their more prominent features now will be discussed briefly.

Aspects of the present disclosure include a catheter device that includes a needle having a needle tip and a wall, a notch formed through the wall of the needle proximal of the needle tip, a catheter hub with at least a partially transparent catheter tube, such as a transparent or a semi-transparent or semi-opaque tube material, having the needle located therein, and a flashback indicator which can be disposed over the notch and/or in the notch. A distal portion of the catheter tube can form a seal with the needle.

The flashback indicator can be positioned inside the catheter tube at a location such that blood flow from the notch changes color of the flashback indicator. The flashback indicator can be positioned on the outside of the needle shaft. The flashback indicator can be positioned on the outside of the needle shaft proximal of the notch or overlapping at least part of the notch to contact fluid flow exiting the needle lumen and out the notch.

The flashback indicator, which can embody a biocompatible filter or other biocompatible material, allows a quick and simple indication of primary blood flashback by viewing through the catheter tube, the change in color of the flashback indicator, without compromising a secondary flashback. To enhance blood visualization through the transparent catheter tube, the flashback indicator could be enhanced by the choice of material, the length of the notch, and the contrast in color. The flashback indicator can be made from a medical grade absorbable material or paper, such as cellulose-based papers. The flashback indicator can be made from Versapor® membrane disc filter material, such as Versapor® 1200. The material can be an acrylic copolymer material. The flashback indicator can be made from a combination of the listed materials.

Although the term transparent is used herein, it is understood that a semi-opaque material falls within the scope of the term provided blood flow or the presence of blood can be viewed through the catheter tube.

A further feature of the present disclosure is needle assembly comprising: a needle hub with a needle comprising a wall surface defining a needle shaft having a needle lumen and a needle tip; a notch formed through the wall surface of the needle proximal of the needle tip; and a flashback indicator is equipped, loaded, or packed with the notch, the flashback indicator having a material that can absorb fluid, change color, or both.

A still yet further aspect of the present disclosure is a needle assembly comprising: a needle hub with a needle comprising a wall surface defining a needle shaft having a needle lumen and a needle tip; a notch formed through the wall surface of the needle proximal of the needle tip, and the notch is equipped, loaded, or packed with a flashback indicator; wherein the flashback indicator having a material that can absorb fluid, change color, or both.

The activator can comprise at least one plunger element configured to be pushed by a male Luer tip. The activator can comprise two spaced apart plunger elements for fluid to flow therebetween. A needle guard can be located between the two plunger elements.

A change in profile can be located along an axial position on the shaft with the notch. In other examples, the flashback indicator can form part of the notch.

The notch can be located proximally of the support element. The support element can include two laterally extending wings.

The notch can be located outside of the catheter tube. The notch can be located inside a tubing section.

The catheter hub can comprise a Y-site.

The needle with a notch can be located inside a bore of the catheter tube or outside the bore. A transparent or semi-transparent plastic film or sheet can formed around the notch to seal an opening of the notch. The plastic film can also seal in a flashback indicator.

At least one ridge can be formed in the bore of the catheter tube.

The at least one ridge can include a width and a length and wherein the width can be wider than a width of the notch.

The length of the ridge can be longer than a length of the notch.

The at least one ridge can contact the needle shaft. Where two or more ridges care incorporated, one or more than one of the ridges can contact the shaft.

The flashback indicator can be made from at least one of a cellulose acetate material, a colloid material, a cotton material, a fibrous material coated with an amphipathic material comprising carboxylates ($RCO_2$), sulfates ($RSO_4$), sulfonates ($RSO_3$), or phosphates, an acrylic copolymer material, or combinations thereof. Part of a flashback indicator can be positioned at least partly inside the notch and part of the flashback indicator can be wrapped around an exterior of the needle shaft.

The flashback indicator can embody a sheet wrapped around an exterior of the needle shaft. The flashback indicator can wrap around the shaft about 1.1 times to about 4 times around the shaft. In other examples, the flashback indicator can wrap around the needle shaft more than 4 times. In still yet other example, the flashback indicator can wrap around less than a full wrap around the needle shaft.

The sheet of the flashback indicator can comprise a proximal edge and wherein the proximal edge of the flashback indicator can be located proximally of the proximal edge of the notch.

The at least one ridge can blocks an opening of the notch.

The at least one notch can comprise two side edges.

A flow channel can be formed by at least one of the two side edges.

A second ridge and a third ridge can be incorporated with the at least one ridge to form two or more flow channels (270).

A first flow space can be located distally of a secondary tipping section and a second flow space can be located proximally of the secondary tipping section.

A recessed section can be formed with the needle shaft for receiving a flashback indicator.

The plurality of ridges can be equally spaced apart from one another inside the bore of the catheter tube or not equally spaced apart.

The catheter assembly can comprise a safety push button for releasing a spring.

The catheter assembly can comprise an elongated housing for receiving the needle following activation of the safety push button.

The catheter assembly can further comprise a fluid port formed with the catheter hub.

A tubing can attach to the fluid port of the catheter hub.

A fluid adaptor can attach to the tubing.

A further aspect of the present disclosure is a needle assembly comprising: a needle hub with a needle comprising a wall surface defining a needle shaft having a needle lumen and a needle tip; an elongated slot formed through the wall surface of the needle and extends a length of the needle shaft and through part of a needle bevel; a tube comprising a bore with at least one ridge formed inside the bore; and wherein the at least one ridge contacts the needle shaft and covers the elongated slot.

The needle with the notch formed through the wall of the needle shaft can be equipped, packed, loaded, secured, applied, or included with a flashback indicator. The flashback indicator can be equipped, packed, loaded, secured, applied, or included inside the notch, partially inside and partially outside the notch, or completely outside of the notch. For example, the flashback indicator can be placed on an outside surface of the needle, proximal of the notch, partially overlapping the notch, or such that it covers the notch.

The flashback indicator can be located in the notch and at least partly in the needle lumen.

The flashback indicator can be partially inside the notch and partially outside the notch or wholly outside of the notch.

The flashback indicator can comprise a distal edge that lies above the notch, aligned with a proximal edge of the notch, or is located just proximal of the proximal edge of the notch.

The bore of the catheter tube can comprise at least one ridge extending inwardly from an interior surface of the bore and extending lengthwise along a length of the catheter tube.

The catheter tube can further comprise a second ridge and wherein the at least one ridge and the second ridge define a flow channel with the shaft.

The catheter tube can comprise a secondary tipping section proximally of a distal opening of the catheter tube.

Two tapered sections can be formed or located on either side of the secondary tipping section.

A sleeve can wrap around the flashback indicator and the notch.

The catheter tube can have an interior surface defining a bore. The bore can have one or more ridges that extend a lengthwise direction of the tube body or can be without any ridge. The ridge can have a width that is narrower than a width of the notch or wider than the width of the notch. The one or more ridges, when incorporated, can extend radially inward so that they contact the exterior of the needle shaft when the needle is located inside the bore of the tube body.

The catheter tube can have a tip section with a distal end opening. Optionally the catheter tube can have a secondary tipping section with two tapered sections on either side thereof. The secondary tipping section can have a reduced outside diameter and reduced inside diameter compared to other sections of the tube body for sealing around the needle shaft.

The flashback indicator can prevent blood from flowing or dropping out the notch. The flashback indicator, when filled with blood, can also prohibit blood from dropping out of the needle tip after the needle has been removed from the catheter tube by maintaining capillary action to keep the blood in the needle at a distal end portion of the needle lumen. The material of the flashback indicator can be hydrophilic to enhance the capillary action.

A valve can be located in an interior cavity of the catheter hub. An activator can also be located in the interior cavity of the catheter hub proximal of the valve to press open the valve.

A needle shield to capture and cover the needle tip when the needle is retracted proximally out the catheter hub can be located at least partially or substantially in the interior cavity of the catheter hub.

The needle shield can also be located in an intermediate hub proximal of the catheter hub. The needle shield can have distal ends that are spaced from the needle shaft, such as placing them on a support structure or a sleeve inside a catheter hub. A change in profile can be provided on the needle to interact with the needle shield.

The flashback indicator can engage and pull the needle shield out of or from the catheter hub. The flashback indicator can be visible through the catheter tube. In some examples, the flashback indicator can be provided with a projection or bump to act as a change in profile to interact with the needle shield or needle guard.

The flashback indicator can be equipped with the notch. The flashback indicator can be located inside the notch, partially inside the notch and partially outside the notch, or outside of the notch, such as on an exterior of the needle shaft. The flashback indicator can have a distal edge that lies above the notch, aligned with a proximal edge of the notch, or is located just proximal of the proximal edge of the notch.

The flashback indicator is understood to be positioned or mounted with a needle, such as being equipped with the needle at or near the notch. The flashback indicator can be mounted inside the notch, partially inside the notch, or completely outside of the notch.

The flashback indicator can facilitate early detection of blood flashback. The flashback indicator can function as a visual indicator to facilitate early detection of blood flashback by changing color. The flashback indicator can provide a luminous effect by changing from a first color to a second color with blood red luminous effect. The first color can be white or off-white.

In an example, a needle assembly is provided with a notched needle and wherein the notched needle is used without a catheter, such as without a catheter tube or a catheter hub. For example, the needle of FIG. 22 may be used without a catheter tube.

Another aspect of the present disclosure includes a method for detecting blood flashback. The method can include providing a needle having a needle tip, a wall defining a needle lumen, a notch formed through the wall of the needle, and a flashback indicator disposed inside the notch and into the needle, inserting the sharp distal end of the needle into a vein such that the flashback indicator is visible outside of the vein, and observing the flashback indicator for the flow of blood flowing within the needle lumen.

Another aspect of the present disclosure is a method for manufacturing a needle assembly. The method can comprise: forming a needle hub with a needle comprising a wall surface defining a needle shaft having a needle lumen, a needle tip, and a notch formed through the wall surface of the needle shaft; equipping the notch with a flashback indicator, the flashback indicator having an absorbent material to indicate presence of a fluid; forming a hub with a catheter tube and projecting the needle through the catheter tube and out a distal end of the catheter tube.

The method can further include inserting the needle through a catheter hub and a catheter tube and extending the needle tip distally of a distal end of the catheter tube.

The method can further include retracting the needle proximally to cover the needle tip with a needle shield.

The needle shield can be supported by a valve opener or an activator located in the catheter hub. The needle shield can also be supported in a third hub located proximally of the catheter hub.

The flashback indicator can engage and pull the needle shield out of the catheter hub, can be bonded to the needle, and can be formed by spraying, coating, or attaching the flashback indicator over the notch.

Yet another aspect of the present disclosure includes a needle device that includes a needle hub, a needle extending from the needle hub and comprising a needle tip, a wall defining a needle lumen, and a notch formed through the wall of the needle at a proximal location of the needle tip, and a flashback indicator disposed inside the notch, wherein blood flowing through the needle is indicated by the flashback indicator. The flashback indicator can engage with a needle guard or shield to remove the needle guard or shield from an interior cavity of a catheter hub.

A still yet further aspect of the present disclosure is a needle assembly comprising: a needle hub with a needle comprising a wall surface defining a needle shaft having a needle lumen and a needle tip; a notch formed through the wall surface of the needle proximal of the needle tip; and a flashback indicator disposed in the notch and located, at least in part, inside the needle lumen, the flashback indicator having a material that can absorb fluid, change color, or both.

The needle assembly can further comprise a catheter hub having an interior cavity and a catheter tube and wherein the needle can project through the catheter tube and the notch is located inside the catheter tube.

The needle assembly can further comprise a valve located in the interior cavity of the catheter hub.

The needle assembly can further comprise an activator located in the interior cavity of the catheter hub proximal of the valve, and wherein the activator can be configured to press open the valve.

The needle assembly can further comprise a needle shield for covering the needle tip located in the interior cavity of the catheter hub.

The needle assembly wherein the flashback indicator can be made from at least one of a cellulose acetate material, a colloid material, a cotton material, a fibrous material coated with an amphipathic material comprising carboxylates ($RCO_2$), sulfates ($RSO_4$), sulfonates ($RSO_3$), or phosphates, or combinations thereof.

The needle assembly, wherein the needle shield can be located in an intermediate hub proximal of the catheter hub.

The needle assembly wherein the flashback indicator can be provided with a protrusion for engaging the needle shield.

The needle assembly wherein the flashback indicator can be porous and visible through the catheter tube.

The needle assembly can further comprise a support element having an interior cavity and a catheter tube extending from a distal end of the support element. A catheter hub can couple to the support element via a flexible buffer element. A needle hub can be positioned on a proximal end of the catheter hub. A needle can project through the catheter tube. A notch can be located inside the flexible buffer element or the catheter tube. A flashback indicator can be located within or in the notch to indicate a presence of blood.

The needle can couple to the needle hub via a wire, which is attached to a proximal end of the needle and to the needle hub. The flashback indicator, when filled with blood, can prevent blood from dripping out of the needle.

A still yet further aspect of the present disclosure is a method for manufacturing a needle assembly comprising: forming a needle hub with a needle comprising a wall surface defining a needle shaft having a needle lumen, a needle tip, and a notch formed through the wall surface of the needle shaft; placing a flashback indicator in the needle lumen at the notch; forming a catheter hub with a catheter tube and projecting the needle through the catheter tube and out a distal end of the catheter tube.

The flashback indicator can have an absorbent material to indicate the presence of a fluid, such as blood.

The method can further comprise placing a needle guard having a proximal wall with a proximal opening and two resilient arms slidably on the needle shaft.

The method can further comprise a valve for limiting fluid flow through the catheter hub.

The method can further comprise an actuator in dynamic contact with the valve.

The method wherein the flashback indicator can be made from at least one of a cellulose acetate material, a colloid material, a cotton material, a fibrous material coated with an amphipathic material comprising carboxylates ($RCO_2$), sulfates ($RSO_4$), sulfonates ($RSO_3$), or phosphates, or combinations thereof.

The method can further comprise a wire attaching the needle to a hub.

BRIEF DESCRIPTION OF THE DRAWINGS

These and other features and advantages of the present devices, systems, and methods will become appreciated as the same becomes better understood with reference to the specification, claims and appended drawings wherein:

FIGS. 11 and 12 show two different views of a needle with a flashback indicator located proximally of a notch.

FIGS. 21A and 21B are schematic cross-sectional side views of a combination needle and catheter tube of the present disclosure penetrating the vasculature of a patient and blood flowing into the needle lumen and when the needle is retracted into the catheter tube, respectively.

FIG. 23 is a perspective view of a needle with an elongated slot provided in accordance with further aspects of the present disclosure.

FIG. 24 is a perspective view of the needle of FIG. 23 located inside a catheter tube.

DETAILED DESCRIPTION

The detailed description set forth below in connection with the appended drawings is intended as a description of the presently preferred embodiments of needle assemblies provided in accordance with aspects of the present devices, systems, and methods and is not intended to represent the only forms in which the present devices, systems, and methods may be constructed or utilized. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

Figure 1:
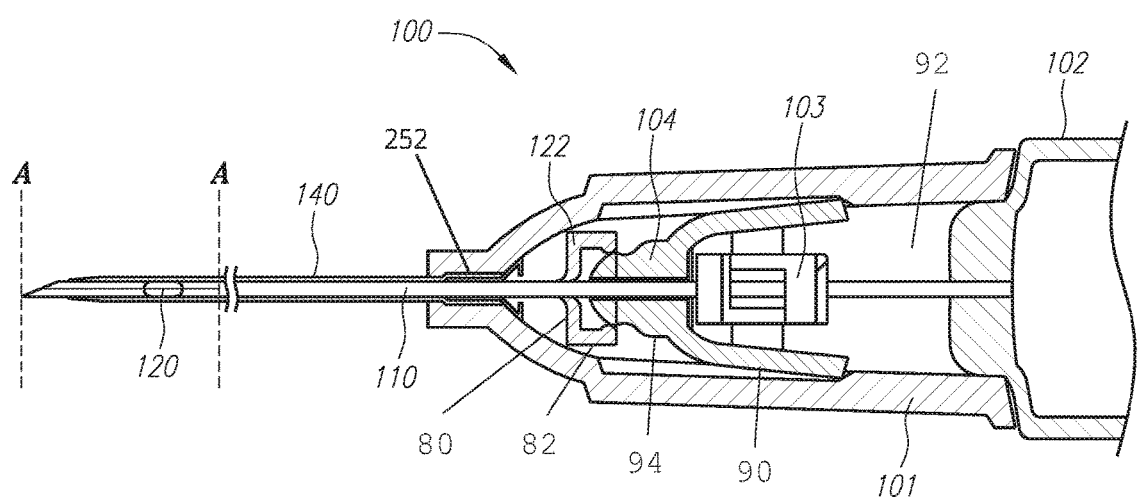
FIG. 1 is a cross sectional view of a safety IV catheter assembly provided in accordance with aspects of the present disclosure.

FIG. 1 shows a catheter device or assembly 100 provided in accordance with aspects of the present disclosure. The catheter device 100 includes a catheter hub 101, a needle hub 102, and a needle 110 projecting through a flexible tube or catheter tube 140. A needle tip 112 with a needle bevel at a distal end of the needle 110 extends out the distal end opening 242 of the catheter tube 140 in a ready position. The needle 110 is understood to have a wall surface defining a needle shaft having a needle lumen. The catheter device 100 can include a needle shield or needle guard 103 to cover the needle tip 112 in a protective position and an activator or actuator 104 for opening a valve 122, which has one or more slits defining a plurality of flaps that can be opened when the activator 104 is advanced by a male medical implement, such as a syringe tip or a Luer adaptor. The needle 110 can include a change in profile 113 (FIGS. 3 and 4), such as a crimp or a radial bulge, incorporated near the needle tip 112 for interacting with a perimeter defining an opening on a proximal wall of the needle guard 103 to stop the needle guard 103 from displacing distally off of the needle. Some needle guards can operate without a change in profile on the needle, such as ones that can cant or slant to grip the needle shaft without a change in profile. The actuator 104 can have a nose section for physically opening the valve 122 and a plunger end comprising at least one plunger element or leg 90 configured to be pushed by a medical implement, such as a male Luer connector. Optionally the valve, valve actuator, and needle guard can be omitted.

The catheter tube 140 is connected to the distal end of the catheter hub 101, which is conventional via a ferrule or bushing 252. The catheter hub 101 defines a hollow interior cavity 92 having the various components mentioned positioned therein. The needle 110 is connected to the needle hub 102 and extends from a distal end of the needle hub 102 and passes through the interior cavity of the catheter hub 101 and into the catheter tube 140 with the needle tip 112 extending out a distal end 242 of the catheter tube 140. The distal portion of the catheter tube 140 can be tapered inwardly or have an opening that has a size smaller than an outer diameter of the needle 110 to form a seal around the opening of the catheter tube 140 with the needle 110 to prevent fluid from entering the space between the catheter tube 140 and the needle 110 when the needle tip 112 pierces the skin of a patient. The space can be annular or can be sectioned by baffles, such as ridges. Blood flowing into the needle lumen when piercing the skin, such as when entering a vein, is known as primary blood flashback. Retraction of the needle tip 112 in a proximal direction into the catheter tube will allow fluid or blood to flow into the space between the needle 110 and the interior of the catheter tube 140, known as secondary blood flashback. The valve 122 is housed within the interior cavity 92 of the catheter hub 16 and when incorporated has the needle 110 projecting therethrough in the ready position shown of FIG. 1.

The valve 122 can include one or more slits forming flaps (not shown) through which the needle 110 extends. In some examples, three slits are provided forming three flaps. In other examples, four slits in the shape of an "X" are provided to form four flaps. Different number of slits and flaps are contemplated. The valve 122 can be seated in a valve seat formed in the interior cavity 92 of the catheter hub. In some examples, bumps or protrusions can be provided around an exterior of the valve to create paths for venting during blood flashback. When the needle 110 is withdrawn from the catheter hub 101 after placement of the flexible tube 14 in the patient's vasculature, the one or more slit closes such that the valve 122 seals upon itself thereby restricting or limiting flow across the valve. The valve 122 thus restricts back bleed through the catheter hub 101. The valve 122 can be constructed of a material that forms a seal or a restriction at the interface with the needle 110 and reseals after the needle 110 is withdrawn. For example, and without limitation, the valve 122 can comprise silicone, silicone rubber, polypropylene, or other suitable materials. Unless indicated otherwise, the various components discussed elsewhere herein may be made from conventional materials.

The activator 104 can be provided to press against the valve 122, such as to project through the slits to open or deflect the flaps, when moved by a medical implement to open the valve 122 to allow fluid or solution to pass through the valve. The activator 104 has a passage formed through the nose section 94 for receiving the needle 110 in the ready position and for fluid flow when the catheter hub is connected to an IV line. The activator can have surface features to provide fluid mixing as fluid enters the catheter hub. After the needle 110 and needle hub 102 are removed, a male medical implement, such as a Luer tip of a syringe, a male Luer connector or adaptor, such as used in connection with an IV line, a Luer access connector, or a vent plug, can be inserted to push the activator 104 distally into the seal 122 to open the seal 122. For example, the activator 104 can be advanced distally by a syringe tip, which presses against the proximal end of a disc 80 of the valve by the activator 104 to push a nose section 94 of the activator 104 distally forward into the valve 122 inside the skirt 82 to open the one or more slits. In an example, the activator 104 can have a wedge shaped nose section 94 to press open the valve 122 and an extension, plunger, or leg 90 extending in a proximal direction from the nose section to be pushed against by a male medical implement. Although a single extension or leg is usable to push the activator 104, two or more extensions are preferred. The extension 90 can embody one or more separate sections that can be pressed against by a male medical implement to advance the activator 104 against the valve 122. Two spaced apart extensions 90 can be provided to accommodate a needle guard therebetween. Examples of activators can be found in U.S. patent application Ser. No. 14/062,081, published as US 2014/0052065 A1, the contents of which are expressly incorporated herein by reference.

In one embodiment, the needle shield 103 is located in the interior cavity of the catheter hub 101 and has the needle 110 passing therethrough. The needle shield 103 is configured to cover the tip of the needle 110 after the needle 110 is withdrawn from the catheter hub 101 to prevent needle stick injuries. Examples of needle shields can be found in U.S. Pat. No. 8,827,965 and in U.S. patent application Ser. No. 13/257,572, published as US 2012/0046620 A1, the contents of which are expressly incorporated herein by reference. These needle shields can be unitarily formed or can be made separately and subsequently assembled together.

The needle shield 103 can be supported by the activator 104. For example, the activator can have a support, a surface, a wall, etc., supporting the needle shield 103. In an example, the activator 104 has a structure, such as a support, that allows the two arms of the needle shield 103 to rest thereon so that the two distal ends of the two arms of the needle shield 103 are spaced from the needle 110 in a ready position. In yet other example, a sleeve may be provide between the two arms and the distal ends of the two arms rest on the sleeve and not on the needle in a ready to use position. Once the change in profile engages the sleeve, the sleeve is pulled proximally to free the two distal ends to move in a radial direction to block the needle tip 112.

Figure 3:
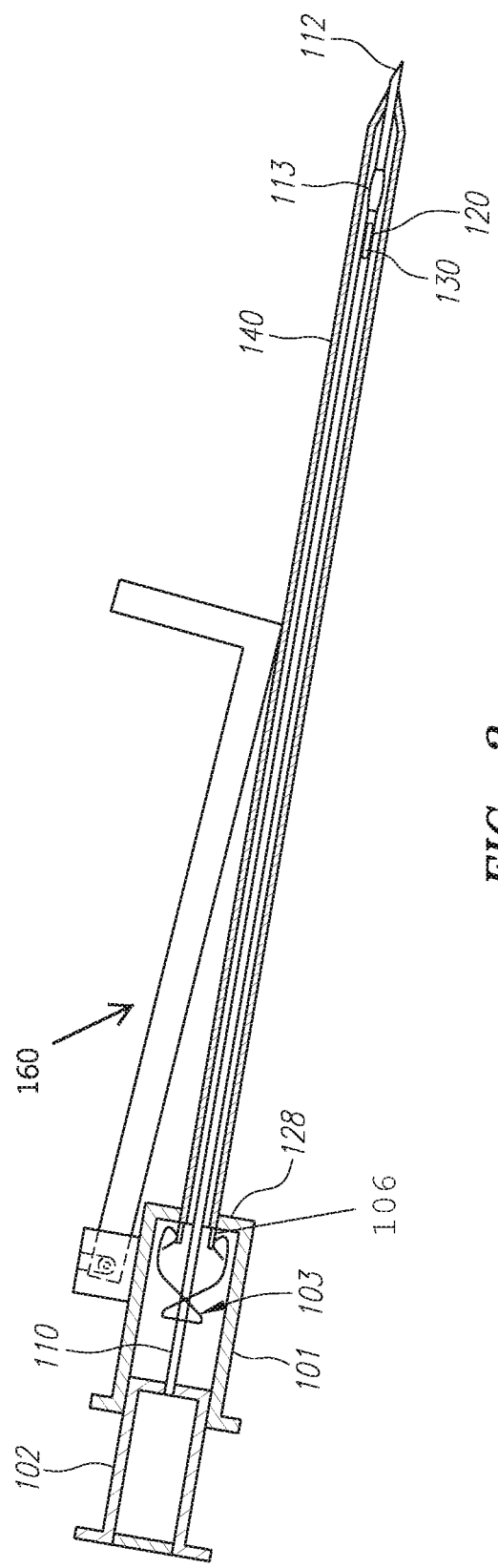
FIG. 3 shows an embodiment of an indwelling needle assembly with a flashback indicator.

Alternatively, the interior cavity 92 of the catheter hub 101 can support the needle shield 103 to keep the two distal ends on the two arms spaced from the needle 110 in a ready position. For example, the catheter hub 101 may be formed as a two-piece body and wherein fins, shoulders, or a sleeve 106 can be provided inside one of the two pieces to support the distal ends of the two arms. Example of a hub support for the needle shield is shown in FIG. 3. The valve 122 can also be modified, such as including only the disc 80 and not a skirt 82, to be positioned in the seam of the two-piece catheter body. In yet another example, the needle shield 103 can be supported or housed in an intermediate hub between the catheter hub 101 and the needle hub 102. The intermediate hub can be removably coupled with the catheter hub 101 and may be referred to as a third hub or a needle shield or needle guard housing.

In still other examples, the catheter hub 101 is provided with a valve that can be actuated with fluid pressure only so that the actuator may be omitted. For example, the valve can flex with head pressure from an IV bag hung on an IV pole pushing up against the valve to open one or more flow paths or channels for fluid flow. In still other examples, the valve is positioned closed to the proximal opening of the catheter hub to be opened by a male Luer connected to the proximal open end of the catheter hub without the actuator or activator 104.

Figure 2:
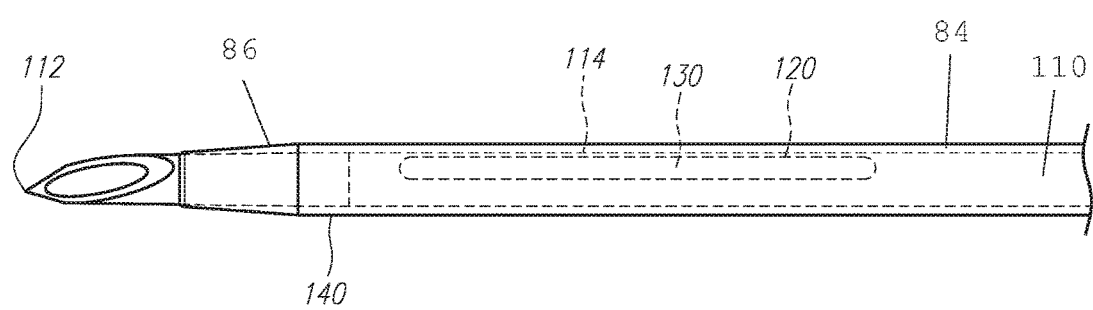
FIG. 2 shows an embodiment of a flashback indicator in a needle notch in a top view.

FIG. 2 is a detail view of section AA of FIG. 1. Specifically, FIG. 2 shows a perimeter 114 defining a notch 120 formed through a wall surface of the needle 110 for instant blood flashback, which could allow blood to flow from the needle lumen out through the notch 120 and into the space 84 between the needle 110 and the catheter tube 140. The space 84 can be annular or not annular depending on whether baffles, such as ridges, are incorporated. The needle 110 may include a change in profile located distally of the notch 120 for interacting with a needle guard. The notch 120 is typically positioned on a side of the needle shaft that allows the needle bevel at the needle tip 112 to face up. In other words, the notch 120 and the needle bevel can be positioned relative to one another so that they can be viewed at the same time.

In the present embodiment, the notch 120 is equipped, loaded, or packed with a flashback indicator 130 to facilitate flashback indication. In an example, the flashback indicator 130 is a plug placed into the notch 120 to prevent or slow fluid flow from passing from the distal needle lumen out through the notch 120. Upon successfully penetrating a vein, blood flowing through the needle tip 112 and into the needle lumen can be confined within a distal needle portion 86 of the needle 110 when the flashback indicator 130 is incorporated. In an example, blood can be trapped by the flashback indicator 130 at the notch 120 and can be thwarted from flowing the length of the needle 110 and out the proximal end of the needle 110 into the interior cavity of the needle hub. In some examples, blood can be slowed to a trickle by the presence of the flashback indicator 130 within the needle lumen at the notch 120. Fluid cannot pass through the notch 120 and into the space 84 when the flashback indicator 130 is in place at the notch 120. In some examples, blood can flow into the space 84 but at a noticeably reduced rate compared to when no flashback indicator 130 is used with a needle 110 having a notch 120. The flashback indicator 130 can be placed into the notch 120 and filled out to the perimeter 114 of the notch 120. In other examples, the flashback indicator 130 can be equipped such as that blood can flow out of the notch 120 from the needle lumen and flow into the space 84 as well as down the needle shaft within the needle lumen and into the interior cavity of the needle hub. For example, the flashback indicator can be placed on an exterior of the needle shaft, as further discussed below.

When the needle device of FIG. 2 is used to perform a venipuncture, early visual confirmation can be made by viewing the flashback indicator 130 through the surface layer of the catheter tube 140. As the flashback indicator 130 gets soaked with blood, such as absorb blood, the flashback indicator changes color indicating the presence of blood. For example, the flashback can change from a first color to a second color. The first color can be a color in which the flashback indicator is dry and the second color can be a color in which the flashback indicator is moist or wet. In an example, the first color can be white or off-white and the second color can be blood red.

The flashback indicator 130 can extend into the needle lumen and act as a plug when soaked with blood, thereby inhibiting blood flow and/or dripping through the needle 110 past the flashback indicator 130 and out the needle proximal opening. Thus, while the presence of blood can be viewed through the catheter tube 140 and at the flashback indicator 130 located at the notch 120, no substantial amount of blood flows into the annular space 84 between the catheter tube 140 and the needle 110 through the notch 120 during the initial stage of catheterization. As previously mentioned, the flashback indicator can also be equipped on the needle to allow flow out of the notch and into the space between the needle and the catheter tube.

Upon retracting the needle tip 112 proximally of the distal opening of the catheter tube 140 following confirmation of primary blood flashback while holding the catheter hub 101 steady so that the catheter tube 140 is located inside a vein, blood can flow into the space 84 to provide secondary flashback indication. With secondary flashback, the presence of the catheter tube 140 and the needle tip 112 being properly positioned inside the vein is confirmed. Thus, an aspect of the present needle assembly is understood to provide instantaneous flashback at the notch 120 of a notched needle while still allowing for secondary flashback indication when the needle is moved proximally relative to the catheter tube 140 by incorporating a flashback indicator 130 at the notch 120. Note that with the flashback indicator 130 at the notch 120, blood flowing into the space 84 between the needle and the catheter tube when the needle tip 112 is retracted does not flow through the notch 120 but instead from the vein directly into the lumen of the catheter tube 140, similar to a non-notched needle. In some instances, it is possible that a relatively small trickle or flow of blood can flow out the notch 120 and into the space between the needle and the catheter tube. Said flow however, is relatively small or highly reduced compared to a notched needle without the disclosed flashback indicator 130.

The needle notch 120 of the present disclosure can be formed using conventional means and can embody any size or shape, such as circular, oval, polygonal, or irregular, but will generally include four edges, including two longitudinal edges and two transverse edges, forming a generally square, rectangular opening, or long ellipse. The needle notch 120 may have rounded or squared corners. The notch 120 can have various sizes while still providing adequate rigidity for performing the medical procedure. Further, as the flashback indicator 130 can provide extra strength to the needle 110, the needle 110 is less likely to bend or kink when performing a venipuncture while still providing visual feedback. Thus, an aspect of the present disclosure could be a notched needle having improved strength and wherein the improvement is provided by a flashback indicator 130 located at least partially inside the needle lumen. Further, the notch 120 should be positioned far enough proximally on the needle tip 112 such that at least a portion of the notch 120 is not inserted into the patient during venipuncture, leaving that portion of the notch 120 outside and visible to the user. In other examples, the notch 120 can be placed closer to the needle tip but wherein early blood flashback can still be detected using a flashback indicator 130 of the present disclosure. For example, by using a wicking effect, the notch can be located outside of direct view but still allow for flashback indication. This leaves a range of placement for the notch 120 anywhere from just proximal of the needle tip 112 to just distal of the catheter hub 101 and preferably proximal of the change in profile 113 (FIG. 3), such as a crimp or a bulge. However, the location of the change in profile 113 is not limited and can be proximal of the notch 120.

The flashback indicator 130 can be made from a hydrophilic or a hemophilic material. When attached or equipped with the needle or when placed inside the needle lumen at the notch 120 and filled with blood, the flashback indicator 130 can function as a visual indicator to facilitate early detection of blood flashback by changing color and can, depending on the compactness and/or density, provide an air tight plug or stopper at the notch, such as when the flashback indicator is soaked with blood. This air tight plug or stopper, when such feature is incorporated, can generate a dead flow space and limit the flow of blood in a proximal direction and back out the distal direction. This in turn prevents blood distal of the flashback indicator 130 from dripping back out the needle 110, similar to covering one end of a filled drinking straw and preventing liquid from draining back out the non-covered end by capillary action. The material of the flashback indicator 130 can be cellulose acetate, colloids, forms of cellulose such as cotton, or other known amphipathic materials or fibers coated with amphipathic materials such as carboxylates ($RCO_2$), sulfates ($RSO_4$), sulfonates ($RSO_3$), or phosphates. A combination of the listed flashback indicators may also be used.

In one embodiment, the flashback indicator 130 provides a luminous effect, which reacts with blood or other biomaterial to indicate the presence thereof. In an example, the flashback indicator 130 is made from a member of the chromogenic polymers which can change its color or optical properties based on the applied stimulus. The applied stimulus could include temperature, pressure, voltage, ion concentration, biochemical reaction, or light to highlight the presence of blood or other fluid. Therefore, the shape and/or choice of material for the flashback indicator can further highlight the presence of blood or fluid. In one embodiment, the flashback indicator 130 is formed and then attached to the needle 110 such as by friction, adhesive, or bonding. In another embodiment, a liquefied material is sprayed on and into the notch 120 and allowed to cure to form the flashback indicator 130 in the notch 120 or adjacent the notch, on an exterior of the needle. The flashback indicator 130 can also be pressed fit into the notch and held thereto by interference. In still other examples, the flashback indicator 130 is placed into or is formed inside a pliable sleeve, forming a sleeved flashback indicator with one or both axial ends of the sleeve flashback indicator exposed for contacting the blood. Optionally, perforations can be provided on the wall or through the wall surface of the sleeve. The sleeved flashback indicator is then pressed into the notch 120 and held there by friction and/or interference.

A cover or coating can be applied to the notch 120 to shield the flashback indicator 130 inside the notch or adjacent the notch. Alternatively, the coating is applied directly to the flashback indicator 130 to prevent blood or other fluid from dripping out the notch 120. This also prevents transferring or wiping blood from the flashback indicator 130 onto another surface if touched. In one embodiment, the coating can be a transparent hydrophobic coating or cover applied over the hydrophilic material of the flashback indicator 130. In another embodiment, the coating is a hydrophilic coating, such as a silicone lubricant to reduce the penetration force of the needle 110.

A sleeved flashback indicator or a flashback indicator with a cover on a needle is further discussed below with reference to FIG. 22. The cover can be a transparent or a semi-transparent plastic placed around the flashback indicator. The flashback indicator can be sheet-like wrapped around the needle shaft. The flashback indicator can absorb fluid, change color, or both.

The flashback indicator 130 and/or the coating applied over the flashback indicator 130 to close in or seal in the flashback indicator 130 inside the needle 110 or on the needle can also act as an enlargement, crimp, or change in profile on the needle 110 to engage a proximal opening of the needle shield 103 during retraction of the needle following successful venipuncture. For example, instead of a separate change in profile, the flashback indicator 130 and/or the coating applied thereover projects radially outwardly from the surface of the needle 110 to form a bulge or a bump. The formed bulge or bump is configured to engage a proximal wall on the needle shield 103 to retract the needle shield 103 out with the needle 110 following successful venipuncture. When retracted with the needle 110, the needle shield 103 covers the needle tip 112 of the needle 110.

In another example, the flashback indicator 130 can instead be smooth or substantially flush with the outside surface of the needle 110 and a separate change in profile is incorporated with the needle 110. In yet another example, no change in profile is incorporated where the needle guard 103 is the type that does not have to interact with the change in profile to protect the needle tip 112, such as the type that cants over to grip the needle 110 using biasing and canting forces or a spring retract type of guard that does not require a change in profile. Thus, the flashback indicator 130 can be understood to extend into or placed at least in part into the lumen of the needle 110, such as the bore of the needle 110, to prevent fluid or gas from passing through the needle lumen when the flashback indicator 130 is filled with fluid, such as blood. Thus, the flashback indicator 130, when filled with fluid, can be substantially air tight to hold the fluid inside the needle 110 distal of the flashback indicator 130. In some examples, the flashback indicator 130 can be porous and can let some trace amounts of blood to leak there past and into a proximal region of the needle 110. In still other examples, the flashback indicator 130 can be mounted adjacent or near the notch to permit normal or near normal flow function out the notch. The flashback indicator can be positioned entirely outside of the needle, such as on an exterior surface thereof, and can still assist with early visual indication of blood flashback.

The flashback indicator 130, when used as a plug, can make the conventional flashback chamber of the needle hub 102 obsolete. Thus there would be no need for the conventional flashback plug, which typically consists of a hard plastic housing and a welded filter membrane. In addition, the needle hub would not need to have a female Luer taper for attaching the flashback plug or a syringe. When not constrained by the opening shape, the needle hub 102 can be made more ergonomic for pulling the needle 110 out of the catheter hub and catheter tube and not to be restricted by the cylindrical shape dictated by the Luer standard. Also deletion of the flash back plug would make the overall product and its packaging shorter. Thus, costs could be saved if the cost reductions of the conventional flashback plug and conventional packaging length are greater than the added costs of the flashback indicator 130 itself.

Referring now to FIG. 3, an example of one embodiment of an indwelling needle assembly 160 having a flashback indicator 130 proximal of the change in profile 113 similar to that of FIG. 2 is shown. The indwelling needle assembly 160 can include a needle hub 102 having a needle 110 extending distally through a second hub 101 and through a flexible tube 140. A needle shield 103 is located in the second hub 101. The needle shield 103 can be attached to a support located in the interior cavity of the second hub 101 so that the two distal ends of the needle shield 103 are spaced from the needle 110 in a ready position. The needle 110 has a needle tip 112 and a notch 120 proximal to the needle tip 112. The flashback indicator 130 is placed inside the notch 120. The perimeter 114 of the notch 120 can be abutted by the flashback indicator 130 or sealed by the flashback indicator 130. For example, the flashback indicator can be located outside of the notch, such as formed around the needle shaft, and the distal edge of the flashback indicator can abut, located adjacent to, or can be aligned with a proximal edge of the notch. Presence of blood can be visible at the flashback indicator 130 to indicate to a viewer or user whether blood is present in the lumen of the needle 110, signifying a blood flashback.

Figure 4:
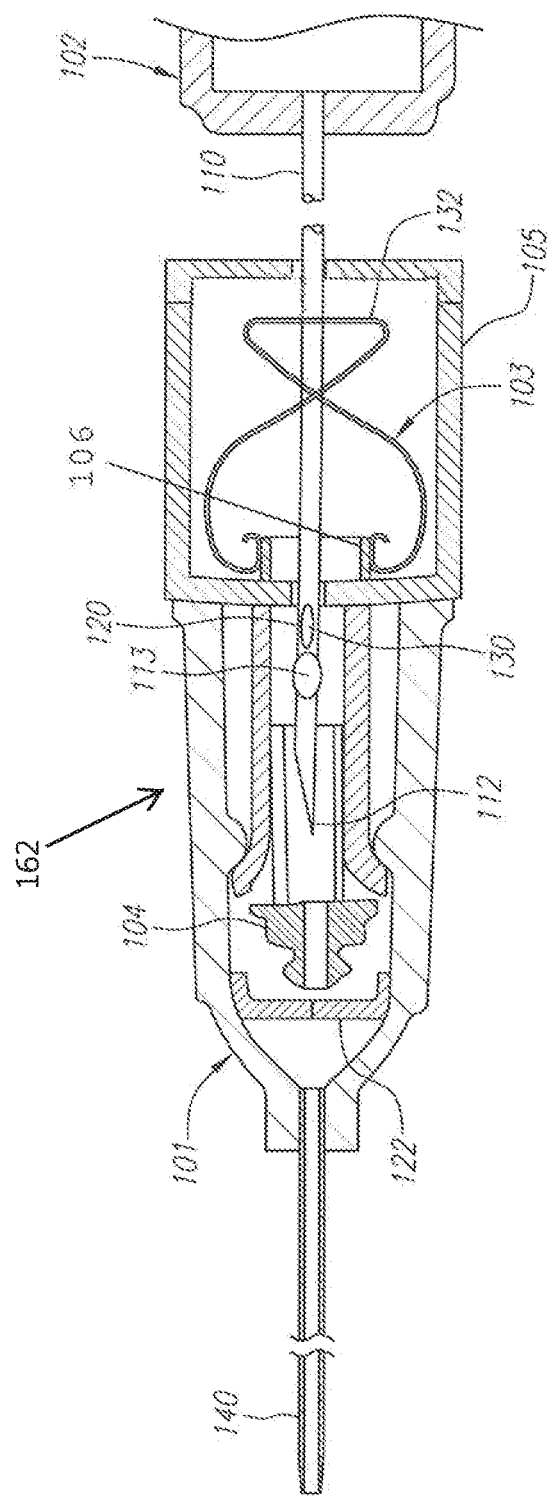
FIG. 4 shows an embodiment of a safety catheter assembly with a flashback indicator in a partially retracted position.

Another example of how a needle 110 with a flashback indicator 130 can be applied or used is shown with reference to the needle assembly of FIG. 4. In FIG. 4, an exemplary safety catheter assembly 162 is shown, similar to the catheter device of FIG. 1 except that the needle safety shield 103, which comprises a biasing or resilient member, such as a resilient arm, is completely outside or substantially outside of the catheter hub 101. As shown, an intermediate hub, a needle shield hub, or a third hub 105 is located, at least in part, between the catheter hub 101 and the needle hub 102. The needle 110 has a change in profile 113, a notch 120, and a flashback indicator 130, similar to other embodiments discussed elsewhere herein.

The needle shield 103 is located on or in the intermediate hub 105. The intermediate hub 105 can be enclosed as illustrated, can have a single wall, or can have openings in the wall. The needle shield 103 can be supported by a sleeve 106 of the intermediate hub 105 or can have the distal arms directly touching the needle 110. The sleeve 106 extends from a distal wall of the intermediate hub 105 so that the resilient arms of the needle safety shield 103 are supported on the sleeve 106. Alternatively, the needle 110 can incorporate a change in profile associated with the flashback indicator 130 or on a cover applied over the flashback indicator 130, such as a projection, for engaging an opening on the proximal wall of the needle shield 103. In use, as the needle 110 is retracted, the change in contour or profile 113 will engage the proximal wall 132 of the needle shield 103 and pull the needle shield 103 proximally so that the two resilient arms are pulled off the sleeve 106 or no longer biasing against the needle 110 and can overlap to block the needle tip 112.

Figure 5:
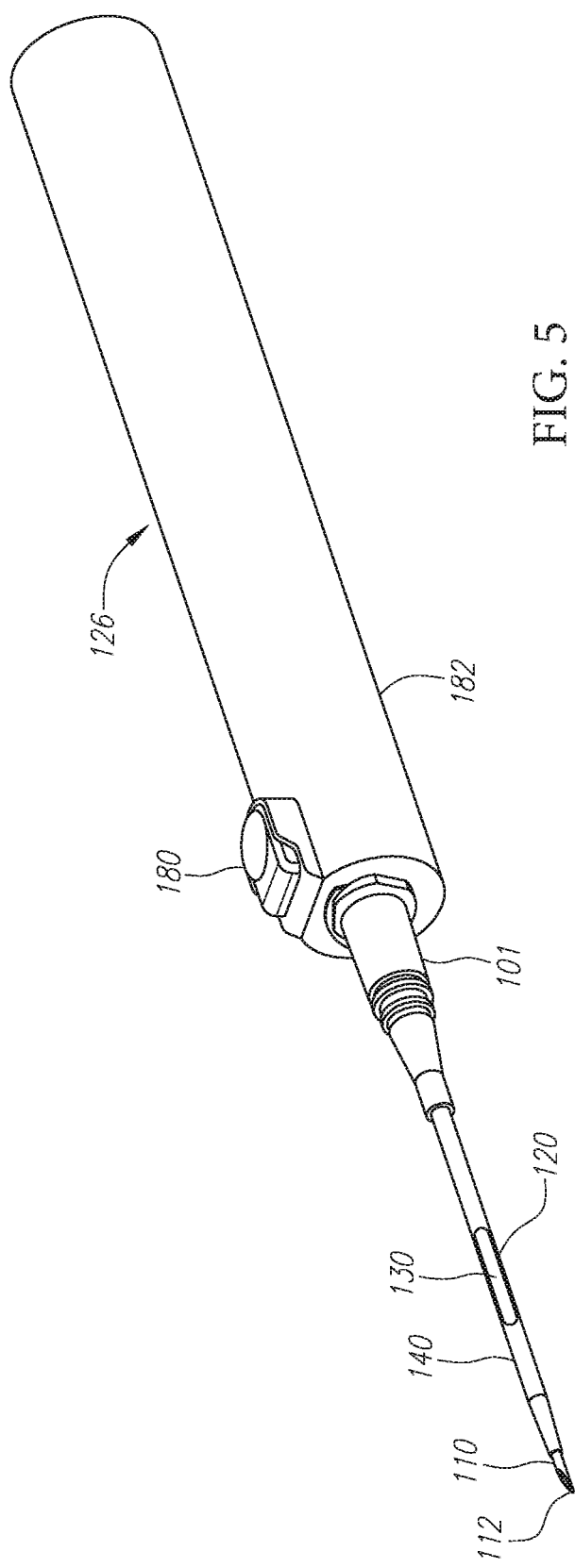
FIG. 5 shows an embodiment of a safety catheter assembly with a safety stop and with a flashback indicator.

Referring now to FIG. 5, a safety catheter assembly 126 having a spring loaded needle carrier that is releasable with or by a safety push button 180 is shown. The needle carrier is attached to a needle 110 comprising a notch 120 and a flashback indicator 130 just proximal of the needle tip 112, similar to needles discussed elsewhere herein. The needle 110 projects through a catheter tube 140, which is attached to a catheter hub 101, and the needle 110 extends out a distal end of the catheter tube 140. After the needle 110 and catheter tube 140 are inserted into a patient, blood flow can be determined by visual feedback at the flashback indicator 130, which changes color to indicate a successful venipuncture. This allows for inspection of blood flow at an earlier point in time during the procedure than typical primary and/or secondary blood flashback. Further, despite incorporating a notch 120 on the needle 110, secondary flashback is still viable as the flashback indicator 130 prevents or limits blood flow out the notch 120 during initial needle penetration and into the space between the needle 110 and the catheter tube 140. The flashback indicator can be equipped with the needle, such as being mounted around the shaft, outside of the notch. The flashback indicator can be partially inside the notch and partially outside the notch, or outside of the notch, such as on an exterior of the needle shaft. The flashback indicator can have a distal edge that lies above the notch, aligned with a proximal edge of the notch, or is located just proximal of the proximal edge of the notch. Once insertion is successful, the needle 110 can be removed from the catheter tube 140 by activating the button 180, which releases a spring that then retracts both the needle carrier, which holds the needle, and the needle 110, into the elongated housing 182 while leaving the catheter tube 140 in place, with the patient.

Figure 6:
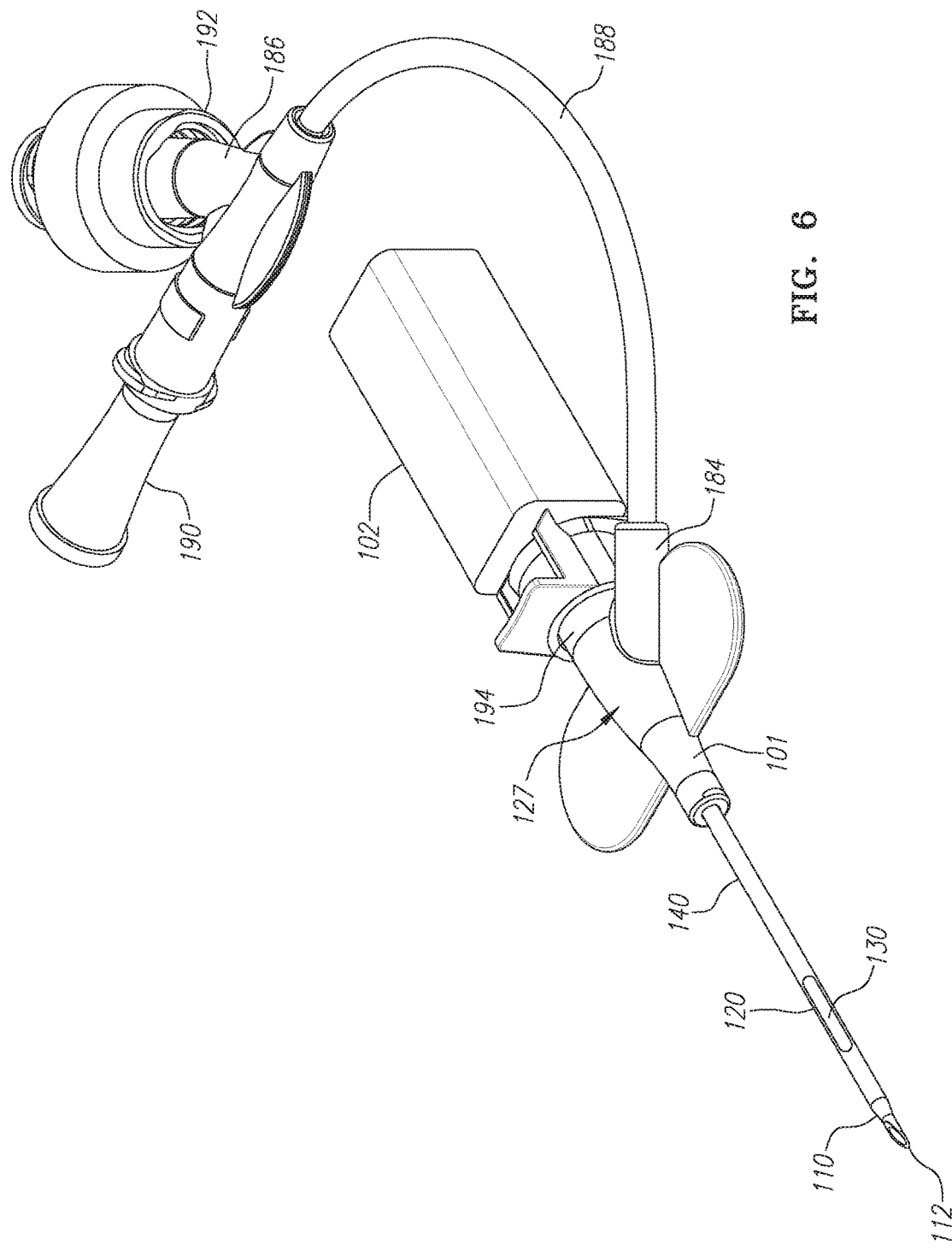
FIG. 6 shows an embodiment of a catheter assembly having an integrated extension line and with an introducer needle assembly with a flashback indicator.

FIG. 6 shows an embodiment of a catheter assembly 127 comprising a catheter hub 101 and a catheter tube 140, a needle hub 102 having a needle 110 extending through the catheter tube 140, a side fluid port 184, and a fluid adaptor 186 attached to the fluid port 184 by a tubing 188 having a lumen for fluid flow between the port 184 and the adaptor 186. As shown, the fluid adaptor 186 is a Y-site comprising at least one needleless female Luer connector 192. The other opening of the Y-site can have a conventional vent plug 190. The proximal end 194 of the catheter hub 101 can be equipped with a septum, a seal or a valve and prevents flow thereacross after removal of the needle 110 and the needle hub 102. A needle shield can be incorporated between the needle hub 102 and the catheter hub 101. The catheter hub 101 is shown with a pair of wings. The needle hub can alternatively have a wing that extends distally along a side of the catheter hub opposite the side fluid port 184, instead of the wing on that side.

A needle tip 112 of the needle 110 extends distally past a distal opening of the catheter tube 140. The needle 110 has a notch 120 and a flashback indicator 130 sealing the notch 120, similar to other needles discussed elsewhere herein. The flashback indicator can also be mounted around the shaft, outside of the notch. Once inserted into the patient, blood flow can be monitored through the catheter tube 140 and indicated by the flashback indicator 130 at or adjacent the notch 120. After successful venipuncture, the needle 110 can be removed from the patient, such as by withdrawing the needle hub 102 in the proximal direction. Fluid can be infused through the fluid adaptor 186, the side port 184, and the catheter. Alternatively if the proximal end of the catheter hub 101 has a valve instead of a septum or a seal, then fluid can be infused through the valve and catheter. A clamp (not shown) can also be used to clamp off the extension line between the side fluid port 184 and the fluid adapter 186.

Figure 7:
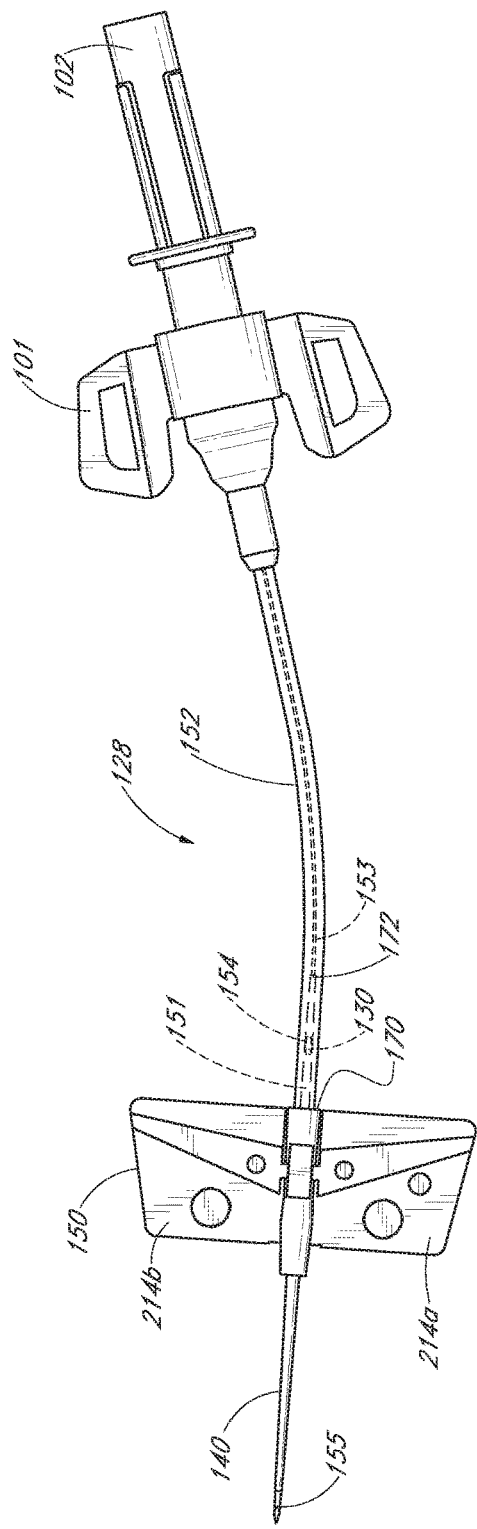
FIG. 7 shows an embodiment of a catheter insertion device having an in-line integrated extension line and a needle with a flashback indicator.

FIG. 7 shows an embodiment of a catheter insertion device 128 comprising a catheter hub 101, a support element 150 having a pair of wings, a flexible buffer element 152 connecting the catheter hub 101 to the support element 150, and a catheter tube 140 extending distally from the support element 150. A piercing needle 151 is disposed in the catheter tube 140 and having a needle tip 155 extending distally of the catheter tube 140. The piercing needle 151 has a proximal end 172 that extends just proximal of the end surface 170 of the support element 150 and terminates inside the flexible buffer element 152. A wire 153 is attached to the proximal end 172 of the piercing needle 151 and at an opposite end to a needle hub 102, which is removably engaged to the catheter hub 101 in a ready to use position. Alternatively, the flexible buffer element 152 can be shorter and the piercing needle 151 would be attached directly to the needle hub 102 without a wire. A flashback indicator 130 is provided in a notch 154 formed with the piercing needle 151, similar to other needles discussed elsewhere herein. Alternatively, the flashback indicator is equipped with the shaft, such as positioned partially inside the notch and partially outside the notch, or outside of the notch, such as on an exterior of the needle shaft. The flashback indicator can have a distal edge that lies above the notch, aligned with a proximal edge of the notch, or is located just proximal of the proximal edge of the notch. The piercing needle 151 with the notch 154 and flashback indicator 130 is similar to other embodiments discussed elsewhere herein except in the present embodiment the notch is located well proximal of the needle tip 155. In some examples, the flashback indicator 130 and the notch 154 of the piercing needle 151 can be located closer to the needle tip 155, inside the catheter tube region. The piercing needle 151 is therefore connected to the needle hub 102 via the wire 153 or is attached directly to the needle hub 102. After successful venipuncture, the needle hub 102 is removed along with the piercing needle 151 and the wire 153 or along with a longer needle with no wire 153. An intravenous (IV) line can then be coupled to the proximal end of the catheter hub 101 to deliver medicinal fluids or IV solution to the patient. The catheter hub 101 can contain a valve, a valve opener, and/or a needle shield as previous explained.

In an example, the wire 153 is connected to the proximal end of the piercing needle 151 by means of welding, bonding, or crimping the open end of the needle 151 to clamp onto the wire 153. If crimping is used to connect the needle 151 to the wire 153, the notch 154 serves as venting and a separate vent hole is not required, although it is optional.

As shown, the catheter hub 101 is separated or spaced from the catheter tube 140 by the flexible buffer element 152, which allows additional comfort to the patient instead of having the catheter hub 101 located adjacent the insertion point of the catheter tube 140. Following successful venipuncture, the support element 150 is taped to the patient adjacent the insertion point to minimize discomfort. This design also allows for a minimum height of the support element 150 as the central portion of the support element 150 is not dictated by the Luer standard. During use, the support element 150 is gripped and manipulated to insert the sharpened needle 151 into the patient's vasculature.

Thus, an aspect of the present disclosure is understood to include a needle assembly comprising: a needle hub with a needle comprising a wall surface defining a needle shaft having a needle lumen and a needle tip; a notch formed through the wall surface of the needle proximal of the needle tip; and a flashback indicator disposed in the notch and located, at least in part, inside the needle lumen, the flashback indicator having a material that can absorb fluid, change color, or both. Alternatively, the flashback indicator can be equipped with the needle shaft, such as partially inside the notch and partially outside the notch, or outside of the notch, such as on an exterior of the needle shaft. The flashback indicator can have a distal edge that lies above the notch, aligned with a proximal edge of the notch, or is located just proximal of the proximal edge of the notch. The needle assembly can further comprise a support element having a catheter tube extending from a distal end thereof, a catheter hub attached to the support element via a flexible buffer element, and a needle hub positioned proximally of the catheter hub; wherein the needle projects through the catheter tube and the notch is located inside the flexible buffer element or inside the catheter tube. The needle assembly wherein the needle can couple to the needle hub via a needle wire or can attach directly to the needle hub without a wire.

Figure 8:
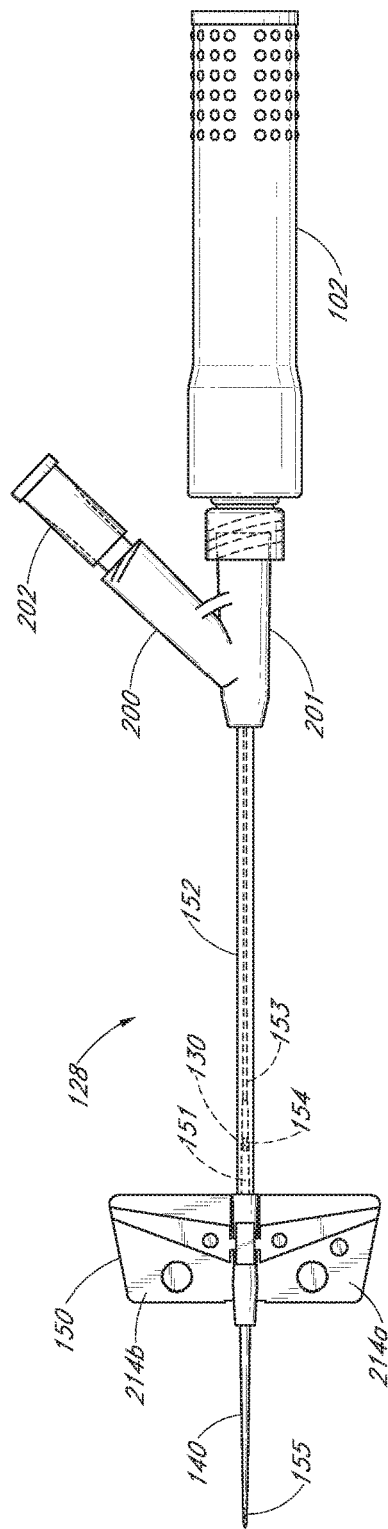
FIG. 8 shows another embodiment of a catheter insertion device with a flashback indicator.

FIG. 8 shows an alternative embodiment of a catheter insertion device 128, similar to the embodiment of FIG. 7 with a few exceptions. In the present embodiment, the catheter hub 201 has a Y-site 200 having a vent plug 202 disposed therein. The vent plug 202 can be removed and an IV-line attached for normal infusion. The catheter hub 201 has a sealed proximal end for sticking with a needle to give bolus injections without removing the drip line. A needle hub 102 can cover a telescoping needle shield, which upon needle removal through the seal extends to cover the piercing needle 151 and lets the wire 153 pass.

Figure 9:
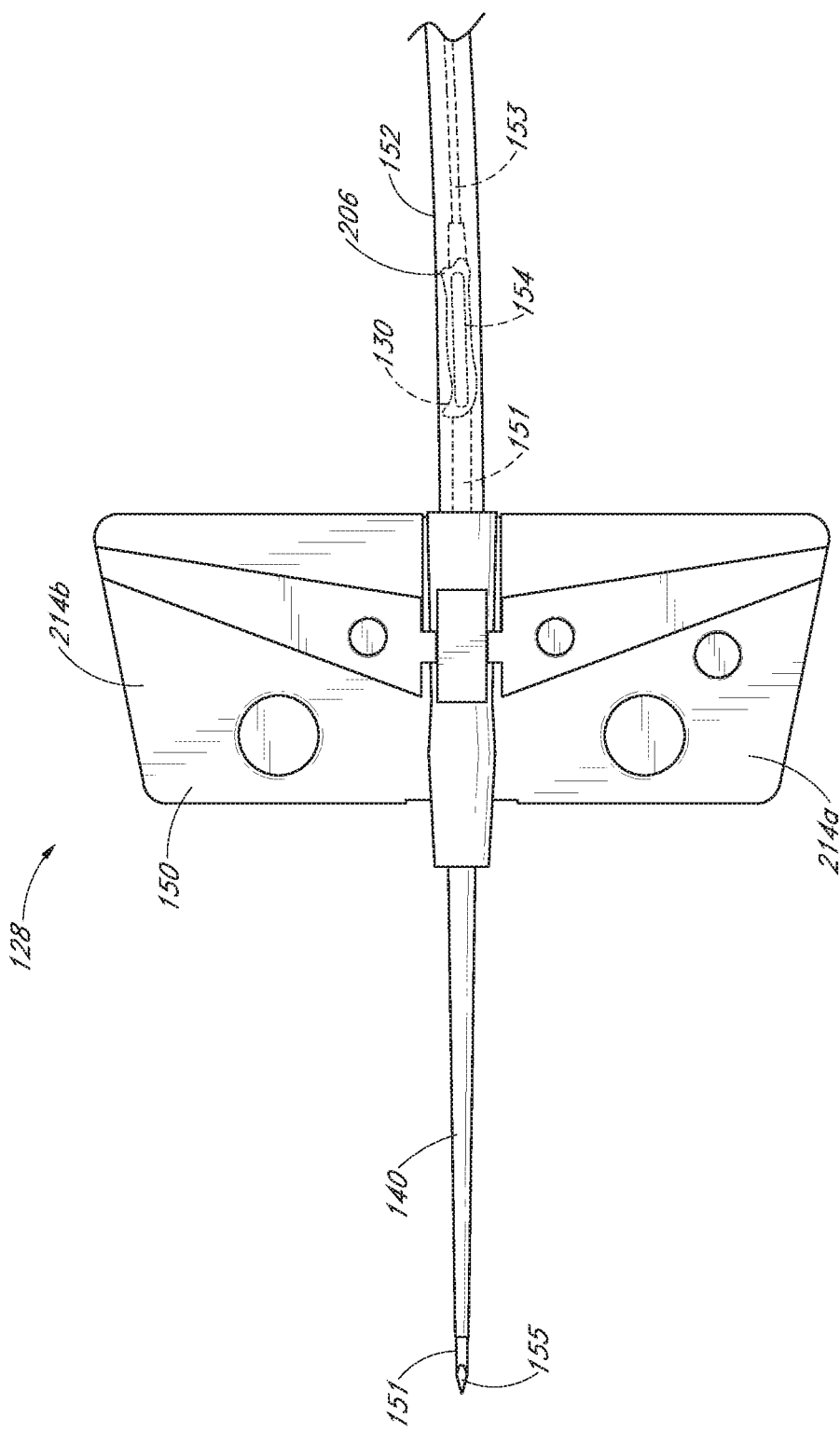
FIG. 9 shows another embodiment of a flashback indicator in a needle notch in a top view.

FIG. 9 illustrates an alternative embodiment of the flashback indicator 130 of FIGS. 7 and 8. The alternative flashback indicator 130 has portions located in the needle lumen and portions 206 extending out of the notch 154. For example, because the flexible buffer element 152 has a relatively larger bore than the catheter tube, additional space is available to accommodate the extended indicator portions 206 that flow outside of the notch 154. Similar to the previous embodiments discussed elsewhere herein, the flashback indicator 130 is configured to indicate a successful venipuncture. In the illustrated embodiments, the flashback indicator 130 is located proximal of the support element 150. However, the flashback indicator 130 may be located elsewhere, such as distal of the support element 150 inside the catheter tube 140. Alternatively, the flashback indicator can be equipped with the needle shaft, such as partially inside the notch and partially outside the notch, or outside of the notch, such as on an exterior of the needle shaft. The flashback indicator can have a distal edge that lies above the notch, aligned with a proximal edge of the notch, or is located just proximal of the proximal edge of the notch. Thus, the presence of blood can be viewed through the catheter tube 140 or the flexible buffer element 152 depending on the placement or location of the flashback indicator 130 and the notch 154. In both instances, a secondary flashback is still available as the needle 151 is pulled into the catheter tube 140 and the catheter tip of the catheter tube 140 is advanced into the vein or artery.

Figure 10:
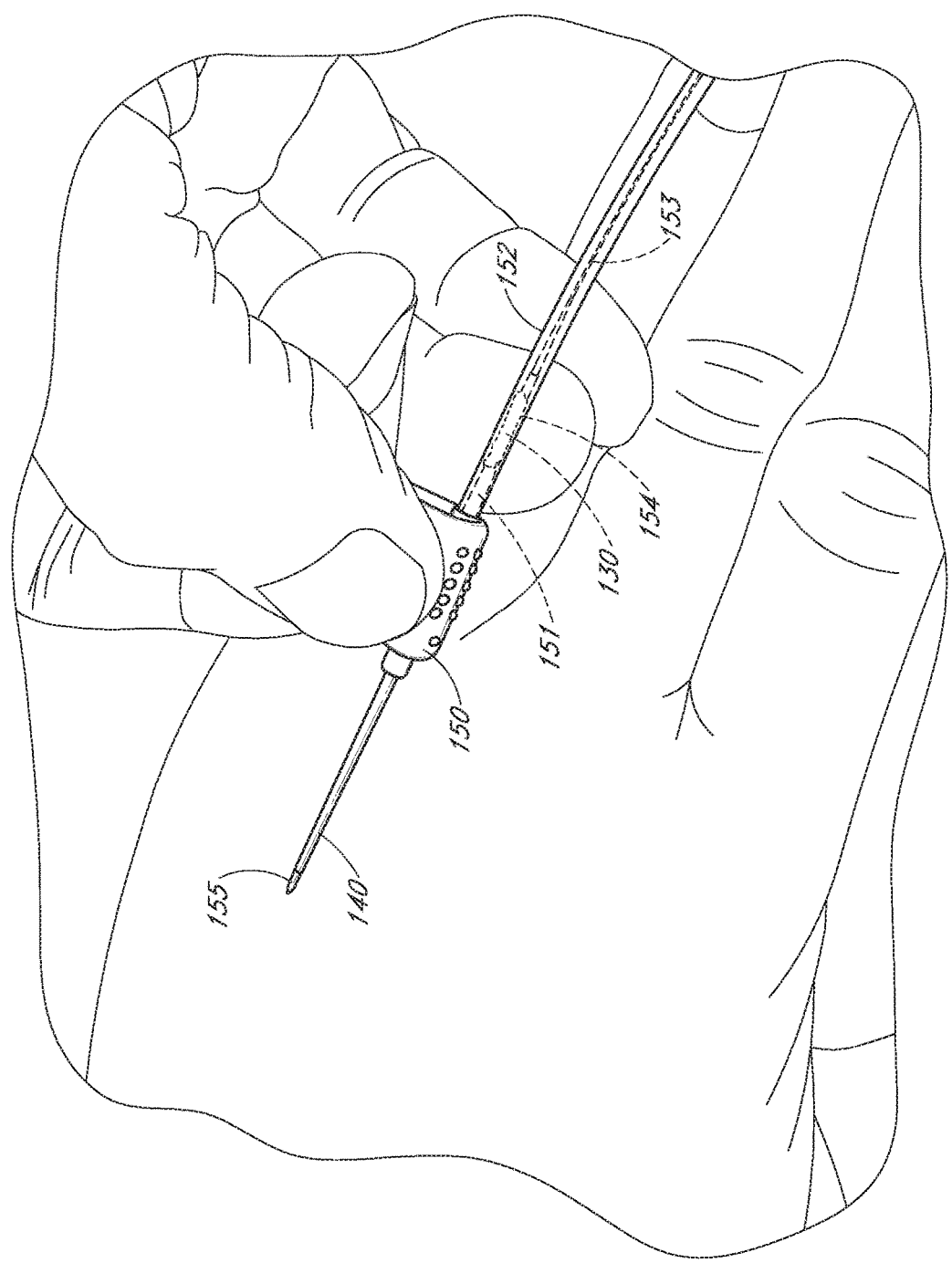
FIG. 10 shows the catheter insertion device of FIG. 7 or 8, to be inserted into a patient.

Referring now to FIG. 10, the device of FIG. 7 or FIG. 8 is shown being used to perform a venipuncture. The wings 214a, 214b are shown gripped and used to grab the needle inside the support element to penetrate the skin with the needle tip 155 of the piercing needle 151. Once the piercing needle 151 is inserted into the patient, blood flow can be determined by viewing the flashback indicator 130 at the notch 154 or adjacent the notch, through the flexible buffer element 152, which may alternatively be viewed through the catheter tube 140 when the notch 154 and the flashback indicator 130 are located therein. After successful venipuncture, the piercing needle 151 can be removed from the patient, such as by withdrawing the piercing needle 151 in the proximal direction by pulling onto the needle hub 102, which pulls on the wire 153 to retract the piercing needle 151. Fluid, such as blood, can then flow through the catheter tube 140 and the flexible buffer element 152 when the piercing needle 151 is pulled proximally of the distal tip of the catheter tube 140 to provide secondary flashback.

With reference now to FIG. 11, a needle 110 having a needle wall 50 defining a needle shaft 52 is shown. The needle shaft 52 has a notch 120, a needle tip 112 with a needle bevel 238, and a proximal end 54 opposite the needle tip 54. The needle shaft 52 can have a sufficient length and gauge for use in any of the various needle assemblies or devices discussed elsewhere herein. In an example, a change in profile 113 can be provided with the needle shaft for interacting with a needle guard or needle shield 103, as previously discussed. In some examples, the notch 120 can be formed proximally of the change in profile 113 or can be formed at or aligned with the change in profile along an axial position on the needle shaft.

In the present embodiment, a flashback indicator 130 can be provided on an exterior of the shaft 52. For example, the flashback indicator can be equipped with the needle shaft, such as partially inside the notch and partially outside the notch, or outside of the notch, such as on an exterior of the needle shaft. The flashback indicator can have a distal edge that lies above the notch, aligned with a proximal edge of the notch, or is located just proximal of the proximal edge of the notch. As shown, the distal edge 232 of the flashback indicator 130 is placed proximally of a proximal edge 230 of the notch 120. The distal edge 232 of the flashback indicator 130 can be coincident with the proximal edge 230 of the notch. In other examples, the distal edge of the flashback indicator 130 can be located just distal of the proximal edge 230 of the notch or just proximal of the proximal edge 230. The placement and location of the flashback indicator 130 on the outside of the shaft 52 relative to the notch 120 can affect the readiness and speed of which blood flows out of the notch from the lumen of the needle contacts the flashback indicator 130 and changes the color or appearance of the flashback indicator to provide confirmation of primary blood flashback. In some examples, the distal edge 232 of the flashback indicator 130 is located at about a half-way point of the length L of the notch. The notch also has a width W. In other examples, the notch 120 can have a different shape, such as round, and therefore can have one or more edges. In other examples, the notch 120 can have a different opening, such as generally square, oval, or elliptical opening.

In an example, the flashback indicator 130 can be made from a medical grade absorbable paper. In some examples, the absorbable paper can be a cellulose-based paper. The cellulose-based paper can be a cellulose acetate, colloids, forms of cellulose such as cotton, or other known amphipathic materials or fibers coated with amphipathic materials such as carboxylates ($RCO_2$), sulfates ($RSO_4$), sulfonates ($RSO_3$), or phosphates. The flashback indicator can be made from Versapor® membrane filter material, such as Versapor® 1200. The absorbable paper for the flashback indicator 130 may alternatively be a polymeric material, and can be a hydrophilic polymeric material. An example of the polymeric material is an acrylic copolymer material such as acrylonitrile-vinyl chloride copolymer membrane, which may be cast on a nonwoven nylon support. A combination of the listed flashback indicator materials may alternatively be used.

The flashback indicator 130 provides a luminous effect when it is contacted by and reacts with blood or other biomaterial to indicate the presence thereof. In an example, the flashback indicator 130 can be made from a member of the chromogenic polymers which can change its color or optical properties based on the applied stimulus. The applied stimulus could include temperature, pressure, voltage, ion concentration, biochemical reaction, or light to highlight the presence of blood or other fluid. Therefore, the shape and/or choice of material for the flashback indicator can further highlight the presence of blood or fluid.

In some examples, the needle shaft 52 is provided with a recessed section 234 for receiving the flashback indicator 130 so that the outside diameter of the flashback indicator 130 is about the same as the outside diameter of the shaft 52. In other examples, the shaft 52 has generally the same outside diameter, other than at the change in profile 113, if incorporated, and the flashback indicator 130 is added to the nominal shaft section. The outside diameter of the flashback indicator 130 in this alternative embodiment can therefore be larger than the nominal outside diameter of the needle shaft. In some examples, the length of the flashback indicator 130 can be about 6 mm with variation of about plus or minus 3 mm being acceptable. In other examples, the flashback indicator can be longer. The flashback indicator 130, in paper form, can wrap around the shaft once in a single ply or less than once, such as wrapped around about 50% or 75% and up to 99% of the circumference of the shaft. In other examples, the flashback indicator can wrap completely around the shaft once or more than once, such as more than one revolution. For example, the flashback indicator can wrap around the shaft about 1.1 times to about 4 times. In other examples, the flashback indicator can wrap around the needle shaft more than 4 times. In general, more flashback indicator materials provided at or near the notch, such as providing multiple layers of bio-absorbable materials or using a sufficiently thick plies of bio-absorbable materials, can allow the flashback indicator to more readily absorb or draw in blood by capillary action to more readily change color when contacted by blood to enhance visual acuity.

FIG. 12 is a side view of the needle 110 of FIG. 11 turned about ninety degrees so that the needle bevel 238 of the needle tip 112 faces upwardly.

Figure 13:
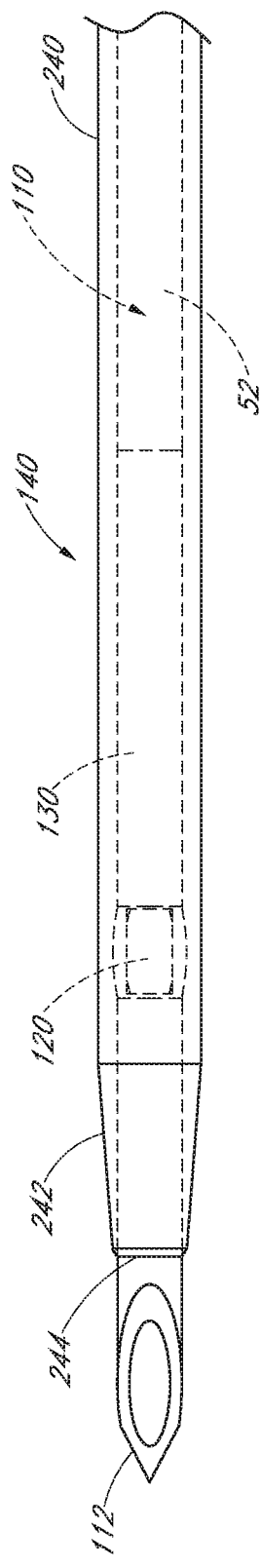
FIGS. 13 and 14 show two different views of the needle of FIGS. 11 and 12 located inside a bore or lumen of a catheter tube.
Figure 14:
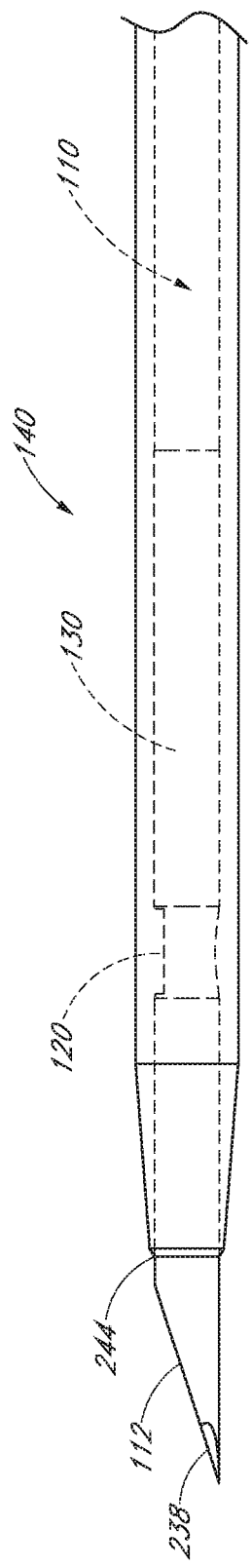

FIG. 13 is a top view of the needle 110 of FIG. 11 located inside the bore or lumen of a flexible tube or catheter tube 140 and FIG. 14 is the same needle 110 located inside the catheter tube 140 but turned about ninety degrees so that the needle bevel 238 of the needle tip faces upwardly. As shown, the catheter tube 140 has a body section or tube body 240 defining a lumen having the needle located therein. The body section or tube body 240 has a generally constant outside diameter and a tip section or area 242 that tapers inwardly into a distal end opening or distal opening 244 having the needle tip 112 projecting outwardly therefrom. The distal opening 244 is reduced so as to form a reduced opening region around the needle shaft 52. In an example, the distal opening 244 forms a seal around the needle shaft 52 and the tapered tip section 242 of the catheter tube 140 facilitates placement of the catheter tube into the vasculature during venipuncture. The combination needle 110 and catheter tube 140 may be used with any of the catheter hubs and needle hubs described elsewhere herein and with or without various valve, valve opener, and/or needle guard.

When in use, blood will flow through the needle lumen and out the notch 120 and into the space between the catheter tube 140 and the needle 110. The blood will then contact the flashback indicator 130. As blood contacts the flashback indicator 130, the color of the flashback indicator will change color to a different color to provide visual confirmation that blood flowed into the needle lumen and out the notch representing successful access of the patient's vasculature. In an example, the flashback indicator is white or off-white in color and upon contact with blood will turn to a blood-red color. This will allow primary flashback to be confirmed at an earlier location or process than at the interior cavity of the needle hub and provide better visual acuity than viewing blood exiting the notch without any flashback indicator through the wall surface of the catheter tube. Further, by employing a flashback indicator 130 of the present disclosure, the flashback confirmation at the earlier location on the needle or earlier process can be more apparent due to the color reaction exhibited by the flashback indicator when blood comes in contact therewith. In other embodiments, features can be added to the combination needle and catheter tube or just the catheter tube of the over-the-needle assembly to preserve secondary flashback, as further discussed below. In some examples, a flashback indicator can be placed inside the needle through the notch and can be wrapped around the exterior of the needle shaft.

Figures 15, 16:
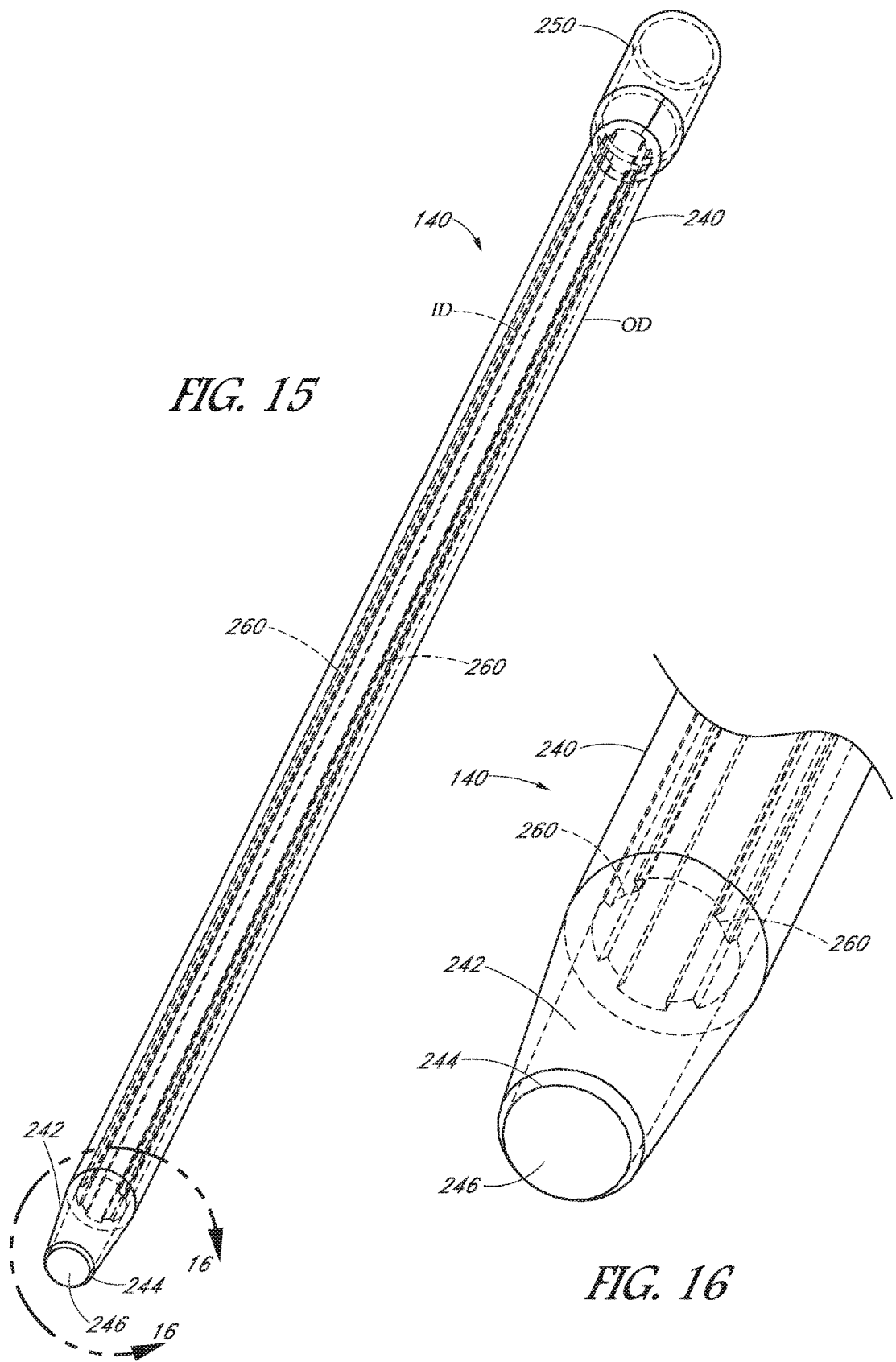
FIG. 15 is a perspective view of a catheter tube in accordance with aspects of the present disclosure.
FIG. 16 is an enlarged partial perspective view of the tip section of the catheter tube of FIG. 15, showing two or more ridges formed inside the bore of the transparent or semi-transparent wall layer of the tube body.

FIG. 16 is a perspective view of a catheter tube 140 provided in accordance with further aspects of the present disclosure, which can be usable with any of the needles 110 having a notch 120 discussed elsewhere herein. As shown, the catheter tube 140 has a tube body 240, a tip section 242 with a distal end opening 244, and proximal base section 250 for use with a ferrule or fitting 252 (FIG. 1) to secure the catheter tube 140 to an interior surface of a catheter hub.

The tube body 240 has an OD along a length thereof and an interior surface defining a bore having an ID, as is well known and understood for any prior art catheter tube. In the present embodiment, two or more spaced apart ridges 260 extend along a length of the catheter tube inside the bore of the tube body 240. For example, two or more ridges 260 can be extruded or molded with the tube body 240 so that they extend inwardly from the interior surface of the tube body 240 along a length or a length portion of the bore. The ridges 240 can form at or near the intersection of the tip section 242 and the tube body 240 substantially along the entire length of the tube body 240 up to about the intersection between the tube body and the proximal base portion 250. In other examples, the length of the two or more ridges 260 can be shorter than the indicated range, such as starting from or near the intersection of the tip section 242 and the tube body 240 and extending to about a mid-way point or a location on the tube body 240 up to about the intersection between the tube body 240 and the proximal base section 250. As further discussed below, the ridges 260 can be provided inside the bore of the tube body 240 to act as dividers for channeling blood flow. In other examples, one or more ridges can be provided to function as a limiting means or a restriction to limit, restrict, or stop blood flow from coming out of the notch, as further discussed below.

FIG. 16 is a partial perspective view of the catheter tube 140 of FIG. 15 showing the tip section 242 and part of the tube body 240. Also shown is a bore 246 of the tube body 240 having two or more spaced apart ridges 260 located therein. In an example, three or four spaced apart ridges 260 can be provided inside the bore 246. In yet other examples, more than four spaced apart ridges 260 can be provided inside the bore of the catheter tube. The ridges 260 can be evenly spaced apart inside the bore or can be dispersed with different gaps inside the bore of the catheter tube. The two or more ridges 260 can have the same lengths and the same widths or can have different lengths and/or different widths. In an example, each ridge has a width that is approximately the length of an eight degree arc to a twenty degree arc length of a circle. Each ridge 260 also has a height that extends radially away from the interior surface of the hub body 240, or orthogonally to the length. The height can be sufficiently sized or dimensioned so as to contact the exterior surface of the needle shaft when the needle is positioned inside the catheter tube 140. In some examples, the height of each ridge 260 can be sized so as to press against the needle shaft to seal against the needle shaft. In other examples, the height of each ridge 260 can come close to but not contact the needle shaft. Where there are two or more ridges 260 provided inside the bore 246 of the catheter tube 140, all of the ridges can contact or press against the needle shaft, some of the ridges can contact or press against the needle shaft, or none of the ridges contact the needle shaft. The spaces between the ridges 260, the needle shaft 52, and the interior wall surfaces of the tube body 240 define flow channels, as further discussed below.

Figure 17:
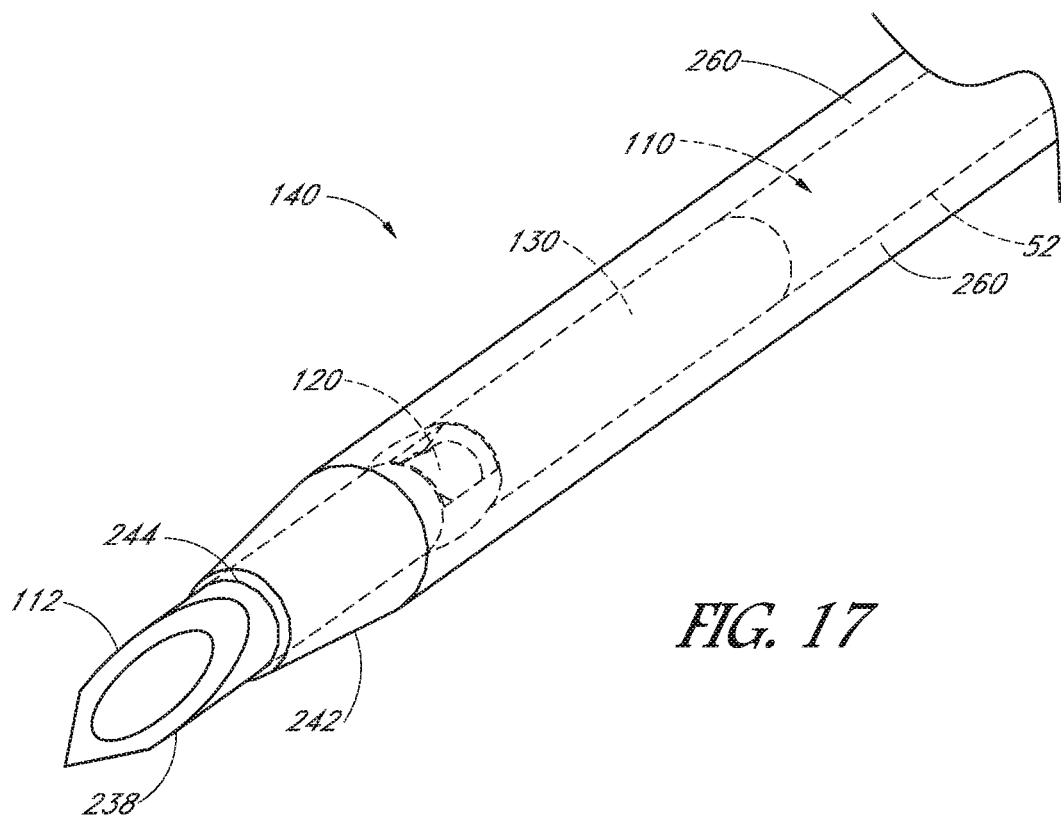
FIG. 17 shows a needle located inside the bore of the catheter tube of FIG. 15.

FIG. 17 is a partial perspective view of a needle 110 having a notch 120 and a flashback indicator 130 of the present disclosure located inside the catheter tube 140 of FIGS. 15 and 16 with the needle tip 112 extending distally of the distal end opening 244 of the catheter tube 140. The notch 120 and the flashback indicator 130 of the needle 110 can be seen through the transparent or semi-opaque wall surface of the catheter tube 140. The ridges 260 can also be seen extending in a lengthwise direction inside the bore. The flashback indicator can be equipped with the needle shaft, such as partially inside the notch and partially outside the notch, or outside of the notch, such as on an exterior of the needle shaft. The flashback indicator can have a distal edge that lies above the notch, aligned with a proximal edge of the notch, or is located just proximal of the proximal edge of the notch.

Figure 18:
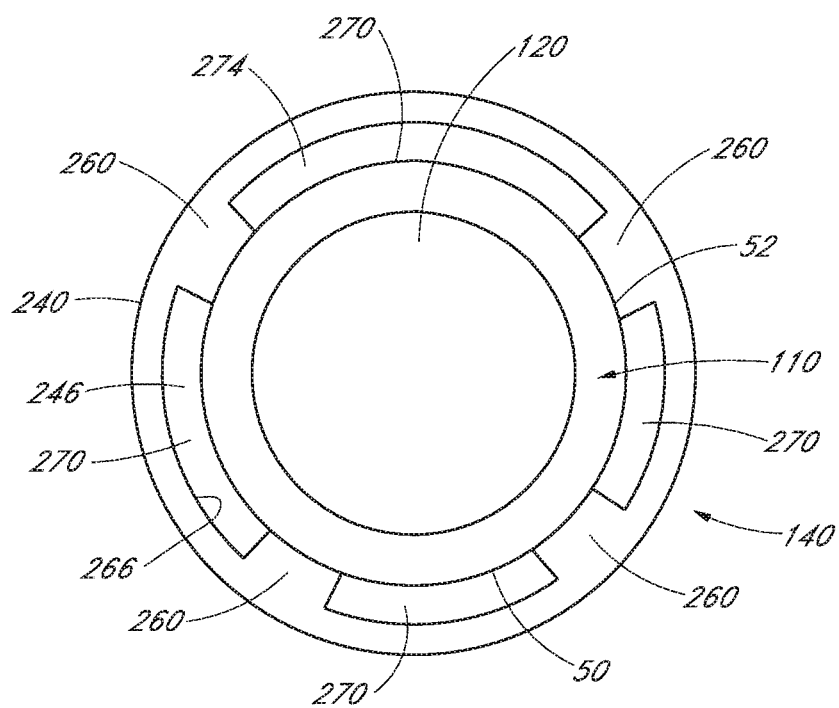
FIG. 18 is a cross-sectional end view of the needle and catheter tube of FIG. 17 taken at the notch.

FIG. 18 is a schematic cross-sectional end view of the assembly of FIG. 17 taken along a section of the notch 120 and looking in the proximal direction. Four spaced apart ridges 260 are shown extending from the interior surface 266 of the catheter tube body 240. The ridges 260 are shown contacting the wall surface 50 of the needle shaft 52. In other examples, only some or none of the ridges 260 contact the wall surface of the needle shaft. As shown, the four ridges 260, the interior wall surface 266 of the tube body 240, and the wall surface 50 of the needle shaft 52 define four spaced apart flow channels 270. In other examples, three ridges 260 or more than four ridges 260 are provided in the bore 246 of the catheter tube 140 to form three flow channels 270 or more than four flow channels 270, which extend lengthwise along the length of the catheter tube. The ridges can be evenly spaced within the bore or be unevenly spaced.

As shown, the notch 120 is aligned with one the flow channels 270. The gap between two adjacent ridges 260 can be wider than the width W of the notch 120 so that the notch is confined between two adjacent ridges 260. The flow channel 270 with the notch 120 aligned therewith may be referred to as a flashback channel 274. That is, during use, blood flowing out of the notch 120 will flow into and down or across the flashback channel 274 in the proximal direction but not freely flow to or into the other flow channels 270 because of the ridges 260, which can act as baffles. Thus, blood flow from the primary flood flashback through the notch 120 and into the space between the needle and the catheter tube can be confined to the flashback channel 274, which is understood to be confined to two adjacent ridges. As the needle 110 is equipped with a flashback indicator 130 at or adjacent the notch 120 on an exterior surface of the needle shaft, the surface color of the flashback indicator 130 can change color and the change can cover a larger surface area of the flashback indicator 130 than to just the width of the flashback channel 274 due to a wicking effect.

Aspects of the embodiment of FIGS. 15-18 include a provision for secondary flashback. That is, upon confirming primary flashback in the flashback channel 274 and the color change of the flashback indicator 130 when accessing the patient's vasculature, changing from a first color to a second color, the needle 110 can be retracted proximally while either advancing or maintaining the catheter tube 140 in the patient's vein. As the needle tip 112 moves proximally and enters the bore 246 of the catheter tube 140, approximately at or just proximal of the intersection between the tip section 242 and the tube body 240 (FIG. 17), blood from the vein will flow through the distal end opening 244 of the tube body 240 and will flow through all of the flow channels 270, including the flashback channel 274, in the space or spaces between the needle and the catheter tube. If so, secondary flashback can be confirmed due to the presence of blood at the other flow channels 270.

Thus, aspects of the present disclosure can include a catheter assembly 100 comprising a catheter hub 102 having a catheter tube 140 and a needle hub 102 having a needle 110 extending therefrom and through the bore 246 of the catheter tube 140 with the needle tip 112 projecting out a distal end opening 244 of the catheter tube 140 (FIG. 1). The needle hub comprises a flashback chamber and the catheter hub comprises an interior wall surface defining an interior cavity. The needle 110 comprises a needle shaft having a notch 120 located proximally of the needle tip and a flashback indicator 130 located inside the notch 120, inside the notch 120 and partly outside the notch 120, or completely outside of the notch on an exterior surface of the needle shaft. The flashback indicator 130 can be separately formed and added to the needle shaft. The flashback indicator 130 has a first color when not in contact with blood and a second color when in contact with blood. The first color can be a light color, such as white or an off-white color. The second color can be color formed when the blood contacts the flashback indicator and changes the color of the flashback indicator. For example, the second color can be a blood red color. The flashback indicator can be one of the flashback indicators discussed elsewhere herein.

The catheter assembly 100 of the present disclosure is configured to provide early primary flashback indicator by bringing forward the primary flashback from the flashback chamber of the needle hub. In an example, the early primary flashback indication is provided by the notch 120, which allows blood to flow from the needle lumen into the space between the needle and the catheter tube. The early primary flashback indication is further enhanced by the flashback indicator 130, which provides a color contrast or visibility that is better or greater than blood red on gray or silver, the typical color of a needle shaft. In the present embodiment, the color contrast or visibility is enhanced by providing a lighter medium or surface for the blood red color of blood to travel over, through, or past to change the color of the lighter medium. This improves visual perception of blood traveling through the notch and into the space between the needle and the catheter tube.

The catheter assembly 100 of the present disclosure is configured to also provide secondary flashback indication. Said differently, for a catheter assembly with a notched needle, the present disclosure includes provisions for preserving secondary flashback, which may not be available for typical prior art catheter assemblies with notched needles. In the present embodiment, secondary flashback can be preserved by incorporating ridges 260 inside the bore of the catheter hub. The ridges can form flow channels and a flashback channel as previously discussed to preserve secondary flashback. Optionally, the flashback indicator 130 can be omitted for catheter assemblies that incorporate one or more ridges 260 and flow channels 270 formed inside a bore of a catheter tube. Such alternative embodiment can provide both early primary flashback indication and secondary flashback indication without also incorporating a flashback indicator 130. In some examples, a change in profile can be incorporated near the needle tip. The change in profile can interact with a needle guard or a needle shield, which can be located inside a catheter hub or in a separate third housing located between the needle hub and the catheter hub, as previously discussed.

With reference again to FIG. 18, the needle 110 can rotate relative to the catheter tube 140 so that one of the ridges 260 straddle or overlie at least part of the notch 120. In other words, there can be instances when the notch 120 is not confined between two adjacent ridges 260. Nonetheless, the assembly of FIG. 18 can still have primary and second flashback indications even when the notch is rotated and not confined between two adjacent ridges 260. For example, where three or more flow channels 270 are formed with three or more ridges 260 and wherein the notch 120 is rotated relative to the catheter tube 140 so that the notch is not confined between two adjacent ridges 260, there can still be at least one flow channel, call a relief channel, in which blood flowing out of the notch 120 from the primary flashback are isolated by the ridges from freely flowing into the relief channel. In other words, even when the needle 110 and therefore the notch 120 is so that the notch is now in fluid communication with two flow channels, a relief channel is still separated from the notch by at least two spaced apart ridges 260. Under that scenario and upon retraction of the needle following venipuncture, blood flowing from the vein and into the catheter tube 140 can flow through the relief channel. Blood flowing through the relief channel can be interpreted as secondary blood flashback.

Figure 19:
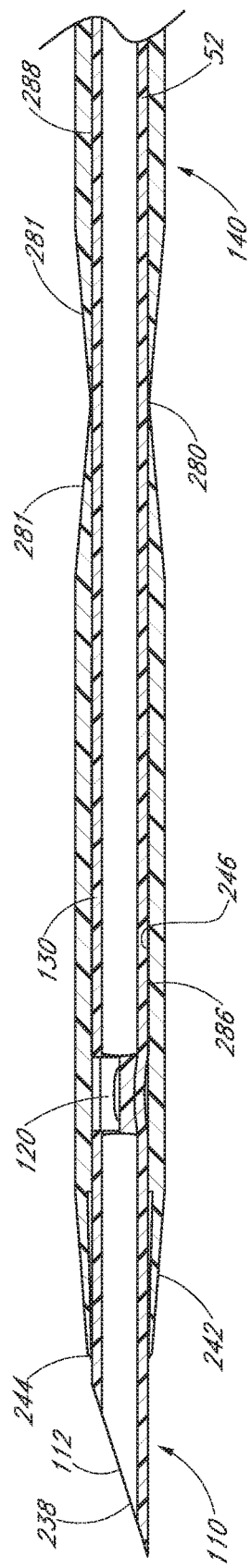
FIG. 19 is a cross-sectional side view of a combination needle and catheter tube provided in accordance with further aspects of the present disclosure.

With reference now to FIG. 19, a cross-sectional side view of a needle 110 located inside a bore 246 of a catheter tube 140 with a needle tip 112 extending out a distal end opening 244 of the catheter tube 140 are shown. The present over-the-needle assembly in which the needle 110 is located inside the catheter tube 140 can be incorporated with a catheter assembly having a catheter hub and a needle hub, such as those shown in FIG. 1. A flashback indicator 130 can be provided on the shaft 52 at or near the notch 120 for enhancing detection of primary blood flashback, as previously described. In the present embodiment, the catheter tube 140 does not incorporate any ridge, such as any of the ridges 260 of FIG. 18. The present assembly can provide primary and secondary blood flashback indications, as further discussed below.

As shown, a secondary tipping section 280 can be provided proximal of the tip section 242 of the catheter tube 140. The secondary tipping section 280 can be a reduced section of the tube body 240 for providing a seal around the needle shaft 52 with the interior of the catheter tube 140. In forming the secondary tipping section 280, two tapered sections 281 can be formed on either side of the secondary tipping section 280, along an axial length of the catheter tube. The secondary tipping section 280 has reduced inside and outside diameters compared to other tube body sections of the catheter tube 140 and can be formed using similar means or techniques for forming the tip section 242 of the tube body 240. For example, the tube body 240 can be heated and then squeezed with one or more dies or molds to form the secondary tipping point 280.

In use, early primary blood flashback through the notch 120 can be detected at the notch and at the flashback indicator 130, as previously described. Optionally, the flashback indicator 130 can be omitted in the present embodiment. Blood flowing out the notch 120 and into the space between the catheter tube and the needle can be confined in a first flow space 286 between the tip section 242 of the catheter tube 240 and the secondary tipping section 280. Then upon retraction of the needle tip 112 following primary blood flashback confirmation, both the needle tip 112 and the notch 120 on the needle shaft 52 can retract in the proximal direction, which provides a path for blood to flow into a second flow space 288 defined by the interior surface of the catheter tube 140 and the needle shaft 52, proximal of the secondary tipping section 280.

Movement of the notch proximally of the secondary tipping section 280 can create different flow profiles or patterns. In a first flow profile, the notch 280 moves proximally of the secondary tipping section 280 before the needle tip 112 moves proximally of the tip section 242 at the distal end of the catheter tube 140. In a second flow profile, the notch 280 moves proximally of the secondary tipping section 280 at about the same time the needle tip 112 moves proximally of the tip section 242 at the distal end of the catheter tube 240. Finally, in a third flow profile, the notch 280 moves proximally of the secondary tipping section 280 after the needle tip 112 moves proximally of the tip section 242 at the distal end of the catheter tube 140. These different flow examples or patterns can be implemented by selecting the placement or location of the secondary tipping section 280 relative to the notch 120 and relative to the needle tip 112.

Under the first flow profile, secondary blood flashback indication may be difficult to detect since it may not be known where the source of blood is flowing from once the notch 120 moves proximally of the secondary tipping section 280 but the needle tip 112 is still distal of the tip section 242 of the catheter tube 140. In other words, blood presence in the second flow space 288 can come from either the vein flowing into the distal open end 244 of the catheter tube 140 or from the lumen of the needle 110 and out of the notch 120 and into the second flow space 288.

Under the second flow profile, blood flowing into the second flow space 288 can only come from the vein flowing into the distal opening and into the bore of the catheter tube 140 since the needle tip 112 is not distal of the tip section 242 of the tube body 240 at the time the notch 120 moves proximal of the secondary tipping section 280. Thus, blood flow into the second flow space 288 can be interpreted or confirmed as secondary blood flashback.

Under the third flow profile, blood flowing into the second flow space 288 can only come from the vein flowing into the catheter tube 140 since the needle tip 112 is not distal of the tip section 242 of the tube body 240 at the time the notch 120 moves proximal of the secondary tipping section 280. Thus, blood flow into the second flow space 288 can be interpreted or confirmed as secondary blood flashback.

Accordingly, aspects of the present disclosure include a catheter assembly having both primary and second blood flashback indications and wherein a catheter tube 140 that surround a needle 110 having a notch 120 has a tip section 242 with a reduced inlet opening at the distal opening 244 compared to the nominal inside diameter of the bore 246 and a secondary tipping section 280 having a reduced inside diameter compared to the nominal inside diameter of the bore. The catheter assembly can further comprise a flashback indicator 130 mounted around the outside of the needle shaft, as previously described. The flashback indicator can be equipped with the needle shaft, such as partially inside the notch and partially outside the notch, or outside of the notch, such as on an exterior of the needle shaft. The flashback indicator can have a distal edge that lies above the notch, aligned with a proximal edge of the notch, or is located just proximal of the proximal edge of the notch. The catheter assembly with the secondary tipping section 280 can have several different flow profiles, as discussed elsewhere herein, in which primary and secondary blood flashback indications can be detected.

Figure 20A:
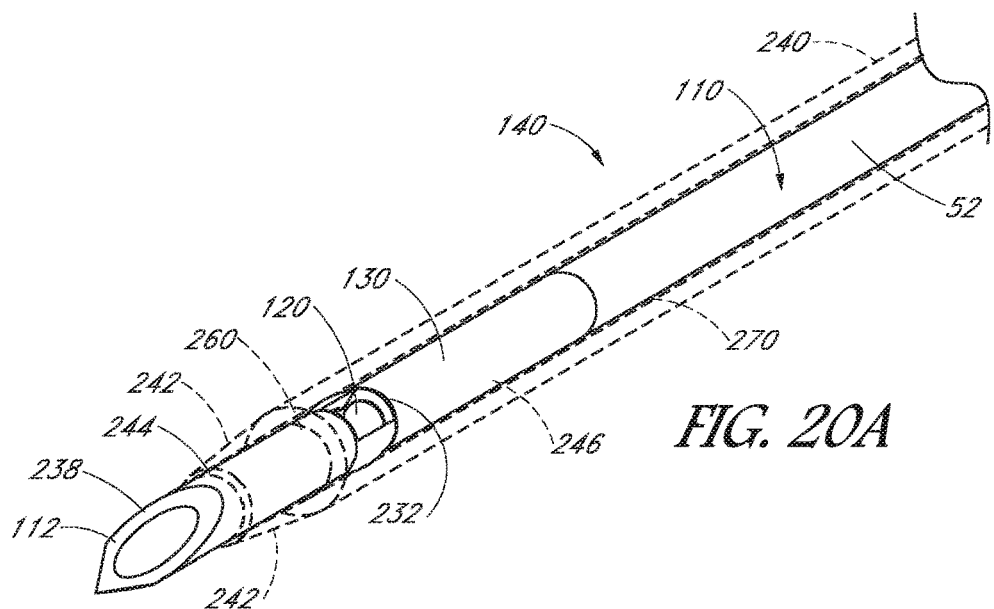
FIG. 20A is a perspective view of a combination needle and catheter tube provided in accordance with further aspects of the present disclosure.

With reference now to FIG. 20A, partial perspective view of a needle 110 located inside a bore 246 of a catheter tube 140 with a needle tip 112 extending out a distal end opening 244 of the catheter tube 140 are shown. The present over-the-needle assembly in which the needle 110 is located inside the catheter tube 140 can be incorporated with a catheter assembly having a catheter hub and a needle hub, such as those shown in FIG. 1. A flashback indicator 130 can be provided on the shaft 52 at or near the notch 120 for enhancing detection of primary blood flashback, as previously described. The flashback indicator can be equipped with a needle shaft, such as partially inside the notch and partially outside the notch, or outside of the notch, such as on an exterior of the needle shaft. The flashback indicator can have a distal edge that lies above the notch, aligned with a proximal edge of the notch, or is located just proximal of the proximal edge of the notch. Optionally the flashback indicator 130 can be omitted. In the present embodiment, the catheter tube 140 incorporates at least one ridge 260, similar to the embodiment of FIGS. 15-18, and can provide primary and secondary blood flashback indications, as further discussed below. In an example, only a single ridge 260 is incorporated with the present catheter tube.

At least one ridge 260 having a width that is wider than the width of the notch 120 is incorporated and extends from the interior wall surface of the tube body 240. The at least one ridge 260 can extend from about the intersection between the tip section 242 and the tube body 240 and can extend up to about the interface between the tube body 240 and the proximal base section or port 250 (FIG. 15) of the catheter tube 140. The at least one ridge 260 with the wide width is configured to seal the notch 120 from free flowing into the bore 246 of the catheter tube 140 during retraction of the needle 110 following successful venipuncture but still allow for early primary flashback detection.

Figure 20B:
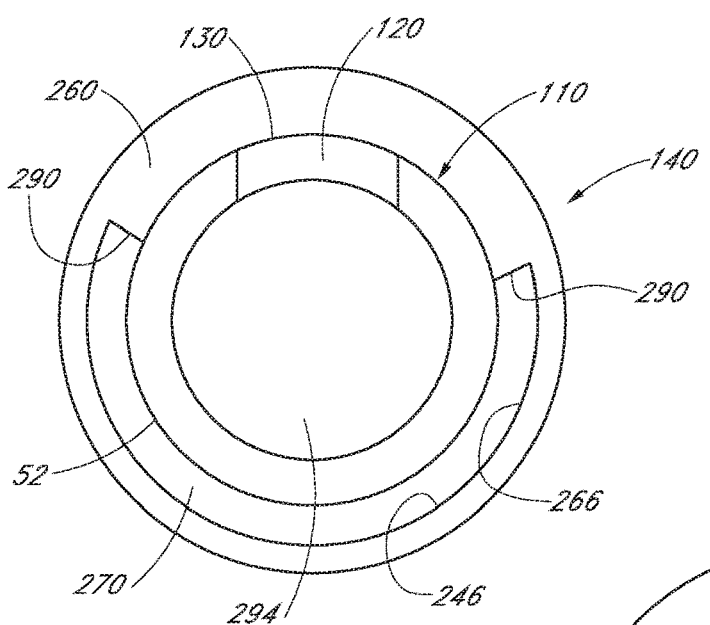
FIGS. 20B and 20C are cross-sectional end views of the needle and catheter tube of FIG. 20A taken at the notch and when the needle tip retracts into the catheter tube, respectively.

FIG. 20B is a cross-sectional end view of the assembly of FIG. 20A taken at the notch 120. With reference to FIG. 20B in addition to FIG. 20A, at least one ridge 260 is formed with the tube body 240 and extends inwardly to contact the needle shaft 52. The contact is sufficient to restrict or limit blood flow from the notch 120 into the flow channel 270 formed between the interior surface 266 of the hub body 240, the needle shaft 52, and two side edges 290 of the ridge 260. Thus, upon accessing the vasculature of a patient, blood flow from the notch 120 is restricted from freely flowing into the flow channel 270 but by placing the distal edge 232 of the flashback indicator 130 in fluid communication of the notch 120, blood can contact the flashback indicator 130 to change its color from a first color to a second color to facilitate early detection of primary blood flashback, as previously described. Additionally, even without the flashback indicator, such as by omitting the flashback indicator, blood can be seen through the wall surface of the tube body 140 at the notch to indicate primary blood flashback at the notch 120.

Upon retraction of the needle tip 112 in the proximal direction following primary blood flashback confirmation, the needle tip 112 will recess into the catheter tube 140 and blood from the vein will enter the distal open end 244 and flow into the flow channel 270. Blood flowing into the flow channel 270 can be interpreted as secondary blood flashback. Because the ridge 260 comprises a length that runs lengthwise of the catheter tube 140, the opening at the notch 120 will continue to be restricted by ridge 260 until the ridge no longer contacts the needle at the notch. Thus, the present over-the-needle assembly having a notched needle can provide both primary and secondary blood flashback indications, with or without a flashback indicator.

Figure 20C:
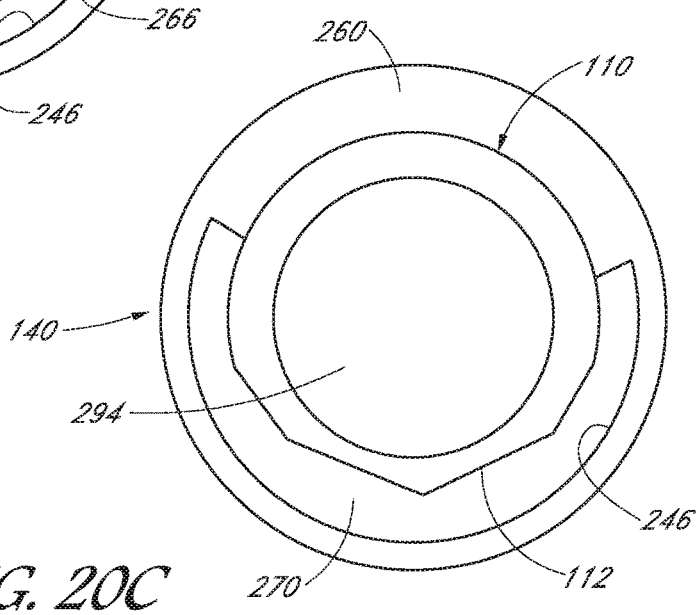

FIG. 20C is a cross-sectional end view of the needle assembly of FIG. 20A showing the needle tip 112 located inside the bore 246 of the catheter tube 140, such as during retraction of the needle 110 following successful venipuncture. Blood from the vein will flow into the flow channel 270 of the catheter tube when the tip section 244 of the catheter tube no longer maintains a seal around the needle 110 and the catheter tube is inside a patient's vein.

FIG. 21A is a schematic cross-sectional side view of a catheter assembly 100 in accordance with aspects of the present disclosure, such as the catheter assemblies of FIGS. 1, 15-18 and 20A-20C, in which the catheter tube 140 has one or more ridges 260 for restricting or confining blood flow from the notch 120 of the needle 110. The assembly is shown following access of the vasculature of a patient and blood beginning to flow into the lumen 294 of the needle 110 and out of the notch 120 proximal of the needle tip 112. Thus, early primary blood flashback detection can be confirmed at the notch 120. Additionally, if a flashback indicator 130 is placed at or near the notch 120, visual indication of early flashback can be enhanced, as previously described.

As shown in FIG. 21A, blood flow out of the notch 120 and into the space between the catheter tube 140 and the needle 110 can be restricted by the presence of a ridge 260 located directly over the notch 120, such as that shown in FIGS. 20A-20C, or by two spaced apart ridges 260 confining the blood flow to primarily a single flow channel or section within the bore 246 of the catheter tube 140, such as that shown in FIGS. 15-18.

FIG. 21B is a schematic cross-sectional side view of the catheter assembly 100 of FIG. 21A with the needle tip 112 retracted inside the catheter tube 140. As shown, blood flow can now enter the distal end opening 242 and into bore 246 of the catheter tube 140 directly from the vein (not shown). As blood flows into the bore, it flows through the lumen 294 of the needle 110 as well as into the empty space or spaces between the needle and the catheter tube. Depending on whether there is one ridge 260 or two or more ridges 260, as previously described, blood will flow into a flow channel 270 or multiple flow channels to indicate secondary blood flashback.

Figure 22:
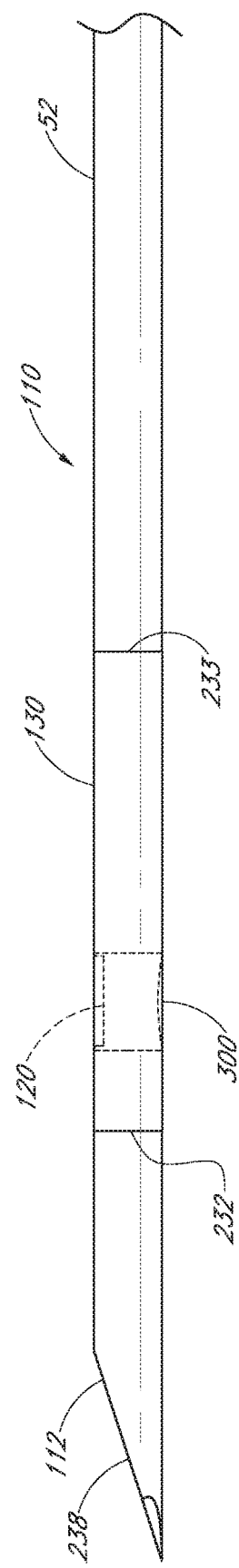
FIG. 22 is a cross-sectional side view of a needle provided in accordance with further aspects of the present disclosure.

FIG. 22 is a side view of a needle 110 having a shaft 52 with a needle tip 112 and a notch 120, similar to other needles described elsewhere herein. The needle 110 is also shown with a flashback indicator 130, similar to other flashback indicators described elsewhere herein. The flashback indicator can be paper-like or sheet-like that is wrapped around the needle shaft. In the present embodiment, the distal edge 232 of the flashback indicator 130 can be located distally of the notch 120, such as distally of the distal edge of the notch, and the flashback indicator 130 is wrapped around the needle shaft 52. In an example, a cut-out can be provided through the flashback indicator 130 to expose at least part of the notch 120 through the cut-out of the flashback indicator. In other examples, the flashback indicator 130 can cover the notch 120 and there is no cut-out to expose the notch.

In the present embodiment, a thin transparent or semi-transparent film 300 is applied around the flashback indicator 130, similar to an over-wrap or a cocoon to encase the flashback indicator 130 and the notch 120. The edges of the film 300 can be sealed, such as by heating, welding, adhesive, or combinations thereof, to form the over-wrap around the flashback indicator 130 and the notch 120. In other examples, a coating can be applied or sprayed onto the flashback indicator. In some examples, the needle shaft 52 is necked down, such as forming a reduced outside diameter section, so that the presence of the flashback indicator 130 and the over-wrap 300 does not protrude out, or least substantially protrude out from the exterior surface of the needle shaft 52. Thus, in an example, the film 300 and the flashback indicator 130, for example at the distal edge 232 and proximal edge 233 of the flashback indicator, are preferably flushed with the exterior of the needle shaft with some protrusion being permissible.

The needle 110 of FIG. 22 is usable with any of the various catheter assemblies discussed elsewhere herein and usable with any of the catheter tubes 140 discussed elsewhere herein, including with any standard catheter tube without any internal ridge. When used with a catheter tube 140 for vascular access, blood flow into the needle lumen will contact the flashback indicator 130 at the notch 120. The flashback indicator 130 will absorb the blood and will change color from a first color to a second color, as previously discussed. Further, due to a wicking effect, the changed color can spread across the surfaces of the flashback indicator 130 so that early blood flashback indicator can readily be recognized, perceived, or confirmed by the changed color. However, any blood exiting from the notch 120 will be confined to within the over-wrap 300 and does not flow into the space between the needle and the catheter tube. Then upon retraction of the needle tip 112 in the proximal direction following confirmation of primary blood flashback, blood from the vein will enter the distal opening of the catheter tube and will flow in the space between the catheter tube and the needle to indicate secondary blood flashback.

The flashback indicator 130 inside the over-wrap 300 can absorb fluid, change color, or both. Fluid, such as blood, can be contained without the over-wrap 300. The needle can be used with or without a catheter tube.

FIG. 23 is a partial perspective view of a needle 110 provided in accordance with further aspects of the present disclosure. As shown, the needle 110 comprises a needle shaft 52, a needle tip 112, an optional change in profile 113, and an elongated slot 310 formed along the length of the needle shaft 52. The elongated slot 310 is preferably formed along the entire length of the needle shaft and on a side of the shaft opposite the sharpened tip 312. The needle 110 of the present embodiment may be used with any of the catheter assemblies discussed elsewhere herein and with any of the catheter tubes having one or more ridges, also discussed elsewhere herein, such as the catheter tube 140 of FIGS. 20A-20C. The elongated slot 310 can have a width that is equivalent to about 6 degrees to 15 degrees of an arc length of a circle. The width of the ridge in the catheter tube can be wider than the width of the elongated slot 310.

FIG. 24 is a partial perspective view of the needle 110 of FIG. 23 located inside a catheter tube 140 and can be part of a catheter assembly having a catheter hub and a needle hub, such as that shown in FIG. 1. In an example, the catheter tube 140 is the same as the catheter tube 140 of FIGS. 20A-20C having at least one ridge 260 that is sufficiently wide so as to extend beyond the two edges of the elongated slot 310. The at least one ridge 260 contacts the needle shaft 52 and limits or restricts blood from freely flowing out of the elongated slot 310 and into the flow channel 270 inside the catheter tube when accessing the patient's vasculature. Primary blood flashback can be confirmed by viewing the blood through the catheter tube 140 and the elongated slot 310 as blood flows into the needle lumen. However, blood flow, if any, will be limited or restricted from flowing into the one or more flow channels 270 inside the catheter tube 140 due to the at least one ridge 260 pressing against the surface of the needle shaft 52.

Following confirmation of primary blood flashback, the needle 110 can be retracted proximally to move the needle tip 112 inside the catheter tube 140. Blood can then enter the distal opening 242 of the catheter tube and into the one or more flow channels 270 inside the catheter tube 140, which can be interpreted as secondary flashback.

Methods of making and of using the needle devices and their components as discussed elsewhere herein are contemplated.

Although limited embodiments of various needle assemblies with a needle having a notch near a needle tip and their components, such as a flashback indicator, have been specifically described and illustrated herein, many modifications and variations will be apparent to those skilled in the art. For example, any over the needle catheter can benefit by using the needle with a notch having a flashback indicator disclosed herein to provide quicker feedback on whether proper needle placement is made without compromising secondary flashback capability to ensure the catheter is properly placed in the blood system. Furthermore, it is understood and contemplated that features specifically discussed for one needle device having a needle notch with a flashback indicator may be adopted for inclusion with another needle device provided the functions are compatible. Accordingly, it is to be understood that the needle devices with a needle notch and their components constructed according to principles of the disclosed devices, systems, and methods may be embodied other than as specifically described herein. The disclosure is also defined in the following claims.

What is claimed is:

1. A needle assembly comprising:
   a needle hub with a needle comprising a wall surface defining a needle shaft having a needle lumen and a needle tip;
   a notch formed as an opening through the wall surface of the needle proximal of the needle tip; and
   the notch is equipped, loaded, or packed with a flashback indicator in contact with the needle shaft,
      wherein the flashback indicator comprises a material configured to absorb fluid, change color, or both at the opening of the notch,
      wherein the material provides a visual feedback overlapping a portion of the opening of the notch when a fluid comes in contact with the material.

2. The needle assembly of claim 1, further comprising a catheter hub having an interior cavity and a catheter tube having a bore and wherein the needle projects through the bore of the catheter tube and the notch is located inside the catheter tube.

3. The needle assembly of claim 2, further comprising a needle shield for covering the needle tip located substantially in the interior cavity of the catheter hub.

4. The needle assembly of claim 2, further comprising at least one ridge formed in the bore of the catheter tube.

5. The needle assembly of claim 4, wherein the at least one ridge has a width and a length and wherein the width is wider than a width of the notch, the length is longer than a length of the notch, and the at least one ridge contacts the needle shaft.

6. The needle assembly of claim 4, wherein the flashback indicator is a sheet wrapped around an exterior of the needle shaft.

7. The needle assembly of claim 2, wherein the flashback indicator, when filled with blood, prevents blood from dripping out of the needle.

8. The needle assembly of claim 2, wherein the bore of the catheter tube comprises a first and a second ridge extending inwardly from an interior surface of the bore, extending lengthwise along a length of the catheter tube, and defining a flow channel with the shaft.

9. The needle assembly of claim 1, wherein the flashback indicator comprises at least one of a cellulose acetate material, a colloid material, a cotton material, a chromogenic polymer, an acrylic copolymer material, a fibrous material coated with an amphipathic material comprising carboxylates ($RCO_2$), sulfates ($RSO_4$), sulfonates ($RSO_3$), or phosphates, or combinations thereof.

10. The needle assembly of claim 1, further comprising a support element having a catheter tube extending from a distal end of the support element, a catheter hub attached to the support element via a flexible buffer element, and the needle hub positioned proximally of the catheter hub; wherein the needle projects through the catheter tube and the notch is located inside the flexible buffer element or inside the catheter tube.

11. The needle assembly of claim 10, wherein the needle is coupled to the needle hub via a needle wire.

12. The needle assembly of claim 1, wherein the flashback indicator is located in the notch and at least partly in the needle lumen, or partially inside the notch and partially outside the notch.

13. The needle assembly of claim 1, further comprising a sleeve wrapped around the flashback indicator.

14. A needle assembly comprising:
   a needle hub with a needle comprising a wall surface defining a needle shaft having a needle lumen, a needle tip, and a needle axis;
   an elongated slot formed through the wall surface of the needle and extends a length of the needle shaft near a proximal end of a needle bevel; and
   a catheter tube comprising a bore with at least one ridge formed inside the bore,
      wherein the at least one ridge of the catheter tube contacts the needle shaft and completely covers the elongated slot to prevent fluid flow between the slot and the bore when viewed along a cross-section of a diameter of the needle.

15. The needle assembly of claim 14, further comprising a catheter hub having an interior cavity attached to the catheter tube.

16. The needle assembly of claim 15, wherein the catheter tube is for infusing fluid, withdrawing blood from a patient, or monitoring various parameters of the patient's vascular system.

17. The needle assembly of claim 15, wherein the catheter hub comprises a valve in the interior cavity.

18. The needle assembly of claim 14, wherein the at least one ridge has a width that is wider than a width of the elongated slot.

19. The needle assembly of claim 14, wherein the at least one ridge of the catheter tube covers the elongated slot to restrict blood flow to prevent free flow into the catheter tube from the elongated slot.

20. The needle assembly of claim 14,
   wherein at least one of the needle and the catheter tube is rotatable between a first position and a second position relative to the other,
   wherein, when the at least one of the needle and the catheter tube is rotated to the first position, the at least one ridge of the catheter tube is configured to contact the needle shaft and completely cover the elongated slot to prevent the fluid flow between the slot and the bore, and
   wherein, when the at least one of the needle and the catheter tube is rotated to the second position, the at least one ridge of the catheter tube does not cover at least a portion of the elongated slot to allow the fluid flow between the slot and the bore.

21. A needle assembly comprising:
a needle hub with a needle comprising a wall surface defining a needle shaft having a needle lumen and a needle tip;
a notch formed as an opening through the wall surface of the needle proximal of the needle tip; and
the notch is equipped, loaded, or packed with a flashback indicator in contact with the needle shaft,
wherein the flashback indicator comprises a material completely covering the opening of the notch configured to absorb fluid, change color, or both at the opening of the notch.

22. The needle assembly of claim 1, wherein the visual feedback is viewed from an angle substantially perpendicular to a length of the needle.

* * * * *